United States Patent [19]
Demarest et al.

[11] Patent Number: 6,073,750
[45] Date of Patent: Jun. 13, 2000

[54] NEEDLE TRANSFER DEVICE

[75] Inventors: David D. Demarest, Parsippany, N.J.; Timothy Lenihan, Morrisville, Pa.

[73] Assignee: Ethicon, Inc., Somerville, N.J.

[21] Appl. No.: 08/804,038

[22] Filed: Feb. 24, 1997

Related U.S. Application Data

[63] Continuation-in-part of application No. 08/715,790, Sep. 19, 1996, Pat. No. 5,727,668, which is a continuation of application No. 08/567,264, Dec. 5, 1995, abandoned, which is a continuation of application No. 08/181,600, Jan. 13, 1994, Pat. No. 5,511,670.

[51] Int. Cl.⁷ .................................................. B65G 47/26
[52] U.S. Cl. ........................... 198/431; 198/803.7; 901/9
[58] Field of Search ..................................... 198/395, 431, 198/448, 606, 803.3, 803.7; 209/540, 542, 559, 564, 903, 939; 901/9

[56] References Cited

U.S. PATENT DOCUMENTS

| | | | |
|---|---|---|---|
| 4,187,051 | 2/1980 | Kirsch et al. | 414/744 |
| 4,437,114 | 3/1984 | LaRussa | 358/101 |
| 4,651,879 | 3/1987 | Harris et al. | 209/903 X |
| 4,674,869 | 6/1987 | Pryor et al. | 356/376 X |
| 4,744,035 | 5/1988 | Hashim | 209/939 X |
| 4,835,450 | 5/1989 | Suzuki | 901/9 X |
| 5,065,237 | 11/1991 | Tsikos et al. | 209/586 X |
| 5,131,533 | 7/1992 | Alpern | 206/63.3 |
| 5,150,307 | 9/1992 | McCourt et al. | 250/223 R X |
| 5,195,234 | 3/1993 | Pine et al. | 29/720 |
| 5,253,765 | 10/1993 | Moorehead et al. | 198/454 X |
| 5,370,216 | 12/1994 | Tsuruyama et al. | 198/395 |
| 5,473,810 | 12/1995 | Demarest et al. | 29/712 |
| 5,542,526 | 8/1996 | Wurgler | 198/803.7 |

FOREIGN PATENT DOCUMENTS

| | | |
|---|---|---|
| 581699 | 2/1994 | European Pat. Off. . |
| 63-299834 | 12/1988 | Japan . |

*Primary Examiner*—Tuan N. Nguyen
*Attorney, Agent, or Firm*—Scully, Scott, Murphy & Presser

[57] ABSTRACT

A needle sorting device includes an infeed device which first singulates a bulk supply of surgical needles into single file with an intermittently driven vibratory feed bowl assembly, and then individually separates and deposits the needles on a first conveyor for transmission to a processing station with a linear slide discharge mechanism. The first conveyor is translucent and during transit, one or more cameras obtain an image of the individual deposited needles. The image is digitized and the digital signals are transmitted to a control system computer which evaluates the position and orientation for needles and processes the information to obtain data for communication to one or more robot assemblies having grippers. Utilizing the position and orientation data, the robot assembly grippers removes selected needles from the first conveyor and transfers each needle to an engagement device located upon a second precision conveyor. This second precision conveyor is provided with additional devices to further orient the needle transferred thereto. A moveable hard stop is provided at the end of the precision conveyor to provide precise positioning of the needle to an accuracy of 0.001 inch at needle hand-off. Each oriented and precisely positioned needle is conveyed by the second conveyor to an automatic swaging station where sutures are automatically attached.

19 Claims, 15 Drawing Sheets

SECTION B-B

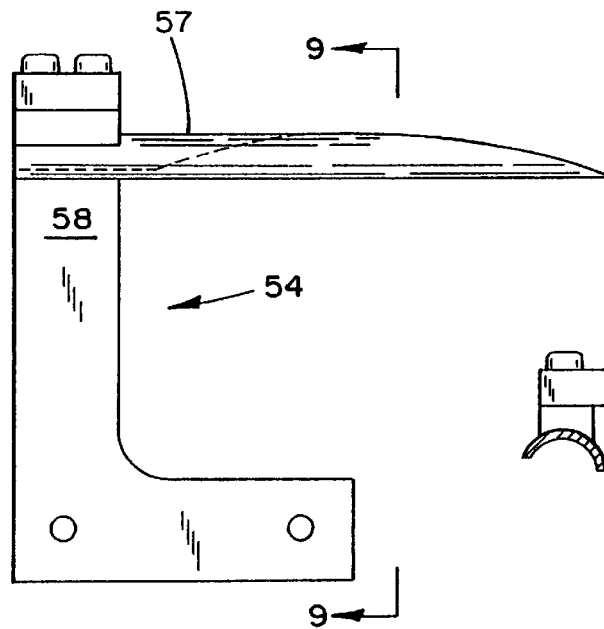
FIG.9(a)
FIG.9(b)
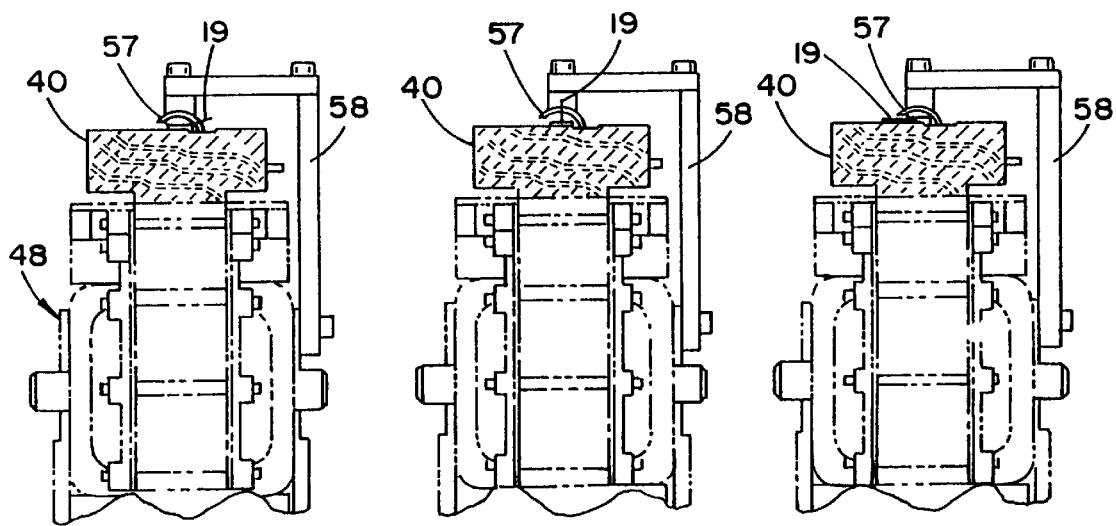
FIG.9(c)　　　FIG.9(d)　　　FIG.9(e)

NEEDLE TRANSFER DEVICE

CROSS REFERENCE TO RELATED APPLICATIONS

This application is a continuation-in-part of U.S. Ser. No. 08/715,790, filed Sep. 19, 1996, now U.S. Pat. No. 5,727,668 which is an FWC of U.S. Ser. No. 08/567,264, filed Dec. 5, 1995, abandoned which is a continuation of U.S. Ser. No. 08/181,600 filed Jan. 13, 1994, now U.S. Pat. No. 5,511,670, all of which are entitled "Needle Sorting Device".

1. FIELD OF THE INVENTION

The present invention relates generally to machines for automatically producing armed surgical needles, i.e., surgical needles having sutures attached thereto, and more specifically, to an infeed apparatus that automatically sorts needles and feeds them for further processing, for e.g., to an automatic swaging device.

2. DESCRIPTION OF THE PRIOR ART

Most armed surgical needles, i.e., needles having sutures attached to one end thereof, that are in present use by surgeons and medical personnel, are manufactured utilizing manual and semi-automated procedures such as those described in U.S. Pat. Nos. 3,611,551, 3,980,177, and 4,922,904. For instance, as described in U.S. Pat. No. 3,611,551, manual intervention is required by an operator to accurately position a suture within the needle for swaging and to adjust swaging dies to increase or decrease swage pressure when suture strands of different gauges are to be swaged. This process is costly in terms of man-hour labor and efficiency because manual positioning is required for swaging to take place.

Presently, suture material may be supplied wound on a bobbin, or, a king or driven spool before being cut and positioned within the swaging end of a surgical needle. In U.S. Pat. No. 3,980,177 the suture material is fed from a spool and taken up on a rotating tension rack where uniform length strands are subsequently cut. Thus, the length of the suture is determined by the size of the rack and manual intervention is required to prepare the rack for the cutting of the suture material wound thereabout. Moreover, manual intervention is required to change the rack each time a suture strand of different length is desired.

In U.S. Pat. No. 4,922,904, the suture material is supplied wound on a bobbin and is fed through various guide means and a heater for straightening the material, prior to insertion within the crimping cavity of the surgical needle. In one embodiment shown therein, an elaborate television monitoring means is required for aligning the drawn suture within the crimping cavity of the surgical needle prior to swaging thereof. In the same embodiment, a rotary encoder device is used to determine the length of suture material unwound from the bobbin prior to cutting. In an alternative embodiment, after swaging of the indefinite length of suture material to the needle, the needle-suture assembly is fed a predetermined distance prior to cutting to obtain a suture strand of predetermined length. Thus, to obtain uniform lengths of suture material every time requires careful manipulations and precise controls, and the processes used to accomplish these tasks are also costly in terms of man-hour labor and efficiency.

U.S. Pat. No. 5,065,237 describes the automatic sorting of mail such as envelopes using conveyors with black and white stripes, a video camera for detecting the edge of a mail piece, and a limited function robotic device for picking up a mail piece based on the leading edge of the mail, but it is not capable of singulating, imaging or sorting surgical needles.

U.S. Pat. No. 5,150,307 discloses a computer controlled sorting apparatus for separating and sorting plastic items having a means for converting an image into digital signals for singulation, but is not capable of determining orientation of needles, the precise placement thereof, or of picking a needle up for placement in a precision conveyor.

U.S. Pat. No. 4,651,879 discloses a bottle sorting station having a conveyor, a transfer device and an engagement device for sorting bottles, but does not singulate from bulk, nor is it able to determine orientation of a surgical needle or provide precise placement of the needle after sorting.

It would be highly desirable to provide an armed needle production and packaging system that is fully automated and that includes means for automatically feeding surgical needles to an automatic swaging machine for the swaging of sutures thereto.

It would also be highly desirable to provide in an armed needle production apparatus, a needle sorting device that can efficiently and accurately orient a needle for subsequent transference to an automatic swaging station.

Even more desirable would be the provision of a control system to maintain the efficiency and integrity of the needle sorting and transferring function.

It would be desirable to provide a needle sorting and singulating apparatus which provides precise pre-positioning of individual needles before imaging to minimize the rejection and recycling of overlapping and nested needles.

It is a further object of the present invention to provide an improved and moveable precise positioning hard stop which will accurately locate the butt end of a curved needle within 0.001 of an inch for hand off to an automatic swaging apparatus.

SUMMARY OF THE INVENTION

Accordingly, it is an object of the instant invention to provide an automatic needle sorting device for singulating and conveying individual needles to a needle processing location.

It is another object of the instant invention to provide a cost effective needle sorting device that virtually eliminates operator exposure to repetitive manual operations.

It is another object of the instant invention to provide an automatic needle sorting device that singulates and positions individual needles in a precise and predetermined orientation for transfer to an automatic swaging station for attaching armed surgical needles thereto.

These and other objects of the present invention are attained with an apparatus for automatically sorting needles and preparing them for automatic swaging and packaging in a reduced size organizer. The needle sorting device comprises at least one receptacle means for holding a plurality of needles, the receptacle means being provided with a means for singulating the needles into a single file of individual needles, and then depositing individual needles on a first translucent indexing conveyor means to provide a moving line of singulated needles for further imaging, manipulation and handling. A first set of remotely located video camera means obtains images of the individual needles upon the first conveyor means and the images are subsequently digitized to enable processing by a control system computer. The digitized signals are processed to obtain both positional and orientation data for individual selected needles on the conveyor. In as much as a curved needle has a sharp point on one end thereof and a butt end on the other end thereof for receiving a suture, it is necessary to determine not only the needles position, but also its orientation.

A robot assembly is provided for transferring individual selected and imaged needles from the first conveyor means to a second precision conveyance means for conveying the needles to an automatic swaging machine.

The control system computer additionally generates instructions for use by the robot assembly based upon the positional and orientation data of the selected unoriented needle. The robot assembly receives the instructions from the control system so that a robot arm may grasp each selected needle and position it in an engagement device located upon the second conveyance means.

One or more orientation devices are provided to ensure that the needles are all uniformly oriented up to within 0.001 of its specified position upon the second conveyor means, so that a transfer for subsequent swaging can effectively take place.

The needle sorting system may also be provided with a second video camera means and a second robot assembly means that operate in the manner as described above on a second conveyor. The redundancy is designed in the system to ensure that a continuous and uninterrupted flow of about 60 needles/minute is supplied to the automatic swaging station.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIG. 9(a) is a side view of the needle rollover (plow) which ensures uniform orientation of the needle on the conveyor boat prior to automatic swaging.

FIG. 9(b) is a front view of the plow taken along line 9—9 of FIG. 9(a).

FIGS. 9(c)–9(e) is a front view illustrating the plow 54 orienting a needle in one direction upon a boat 40 of the precision conveyor.

DETAILED DESCRIPTION OF THE PREFERRED EMBODIMENT

This invention is drawn to a needle infeed apparatus that is designed to automatically singulate, convey and align surgical needles of various sizes to an automatic swaging station where sutures are attached to individual needles.

Figure 1:
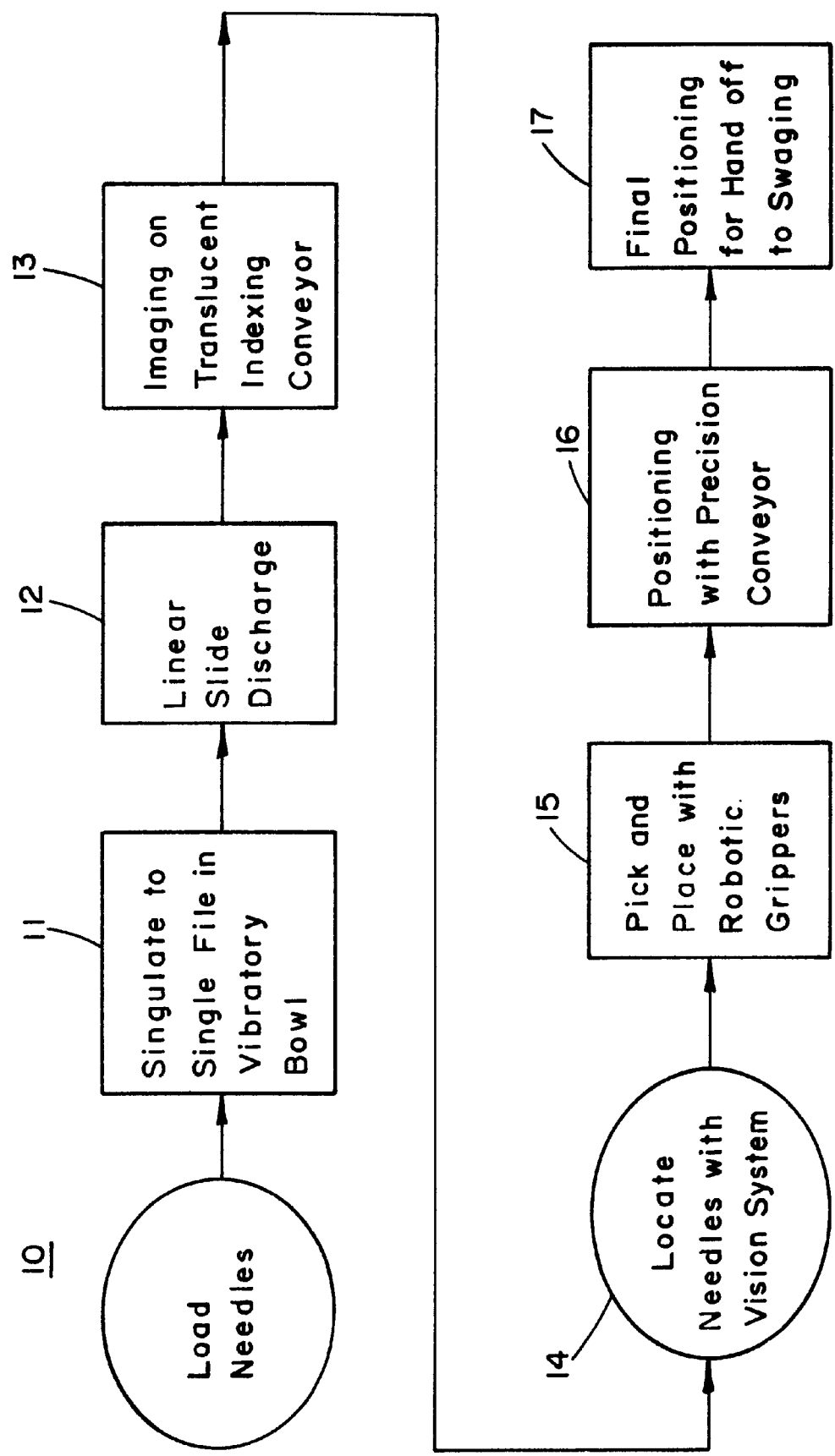
FIG. 1 is a block diagram showing the process flow for the needle sorting apparatus of the present invention.

FIG. 1 is a block diagram generally illustrating the process 10 used to sort needles prior to automatically swaging sutures thereto and prior to packaging them in a reduced size organizer. The automatic needle threading and swaging system and the automatic packaging system of the parent application are both described in further detail in respective U.S. Pat. Nos. 5,438,746 and 5,473,854 assigned to the same assignee of the present invention. As previously mentioned, this invention is drawn to a needle sorting device used to sort, singulate, and convey surgeons' needles of various sizes to an automatic swaging station.

Figure 2A:
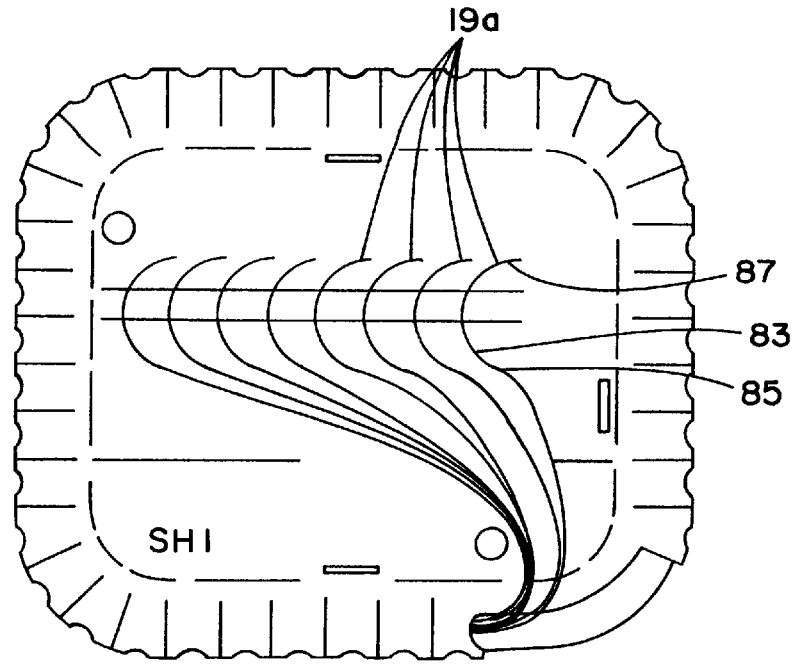
FIG. 2(a) is a diagrammatic view of a reduced size organizer used for packaging needles and sutures which together with FIG. 2(b) illustrate the range of sizes for surgical needles to be handled by the present invention.

FIGS. 2(a) and (b) diagrammatically illustrate the size range of needles to be singulated and positioned for swaging by the present invention. Each reduced size organizer package holds a typical surgical needle 19 having a barrel portion 83, an arcuate blade portion 87, and a suture receiving end or opening 85 for swaging a suture thereto.

The RSO package illustrated in FIG. 2(a) is illustrated with an Ethicon SH-1 needle 19(a) which is 0.018 in diameter and spans an arc of 0.562 inches. The suture to be attached to this needle is 0.0055 to 0.0088 in diameter. The suture opening formed in the barrel of this needle is 0.0106 in diameter, which requires an alignment tolerance of +0.001/−0.0005 when inserting the suture into the needle.

Figure 2B:
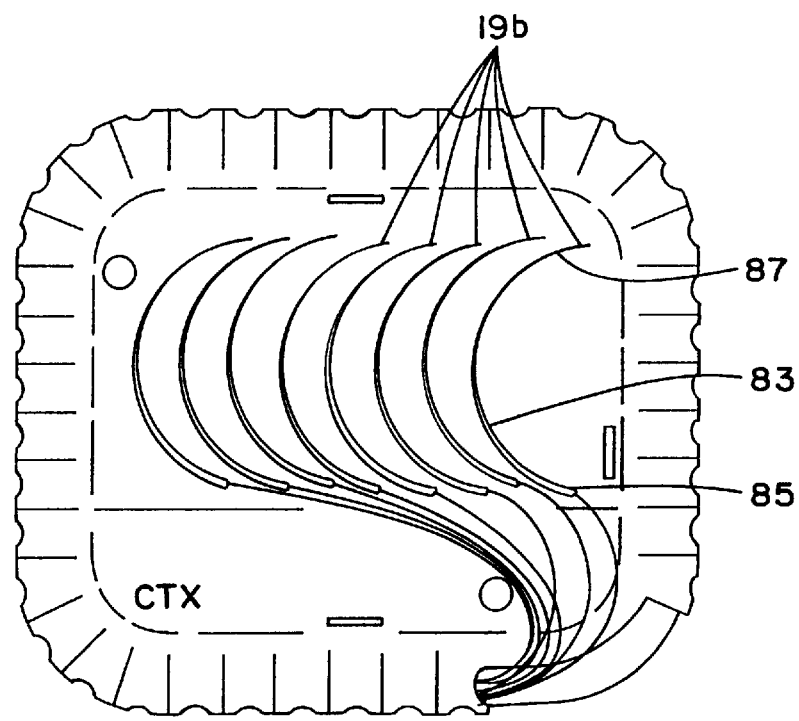
FIG. 2(b) is a diagrammatic view of a reduced size organizer used for packaging needles and sutures which together with FIG. 2(a) illustrate the range of sizes for surgical needles to be handled by the present invention.

The RSO package illustrated in FIG. 2(b) is illustrated with an Ethicon CTX needle, which is 0.050 in diameter and spans and arc more than twice the size of needle 19(b) at 1.3125. The sutures to be attached to this needle are 0.0126 to 0.0176 in diameter. The suture opening formed in the barrel of this needle is 0.0202 in diameter, which requires an alignment tolerance of +0.001/−0.0005 when inserting the suture into the needle.

While the present invention serves the purpose of singulating needles from a bulk manufacturing operation, it also provides a method and means for precise positioning of the needle during the hand-off to a precision multi-axis gripper than will grip the needle and hold it during suture insertion. Thus high precision is necessary in the later stages of the present invention, or the sutures can not be automatically inserted into the needle barrel in the subsequent swage operation.

The packages illustrated in FIGS. 2a,b are primarily intended to illustrate the problems inherent in determining the position and orientation of a wide size range of needles, since an arcuate center grip point on the curved portion of the needles from varies by more than 100% in one dimension, and over a half inch in the other dimension. These variances must be reduced to an accuracy of 0.001 before hand-off of the needle to the swage operation.

In addition to the accuracy of positioning, a correct orientation must be determined. To a convention vision systems the needles appear as arcs with similar ends. However, it is vitally important to determine with the vision system, which end is the barrel end and which end is the sharp end, or the subsequent swage operation will fail.

Generally, in the automatic needle sorting process 10 shown in FIG. 1, needles are first loaded into a vibratory bowl at step 11, automatically singulated into single file and individually fed in a spaced relationship at step 12 to a translucent indexing conveyor. The translucent indexing conveyor allows imaging of the needles 19 at step 13, which images are converted to digital data, and evaluated with respect to orientation and position by a vision tracking system which is part of a computer control system at step 14. After determining position and orientation, the needles are picked up by a robot apparatus at step 15, and transferred to a precision conveyor by the robot apparatus at step 16. At the final step the needles are pre-positioned and then precisely positioned where they are transferred to a multi-axis indexing means for conveyance to subsequent swaging workstation at step 17.

A detailed explanation of the apparatus used to carry out each step will be explained in further detail hereinbelow. A further explanation of the computer control system may be found in U.S. Pat. No. 5,568,593 assigned to the same assignee of the present invention.

Figure 3A:
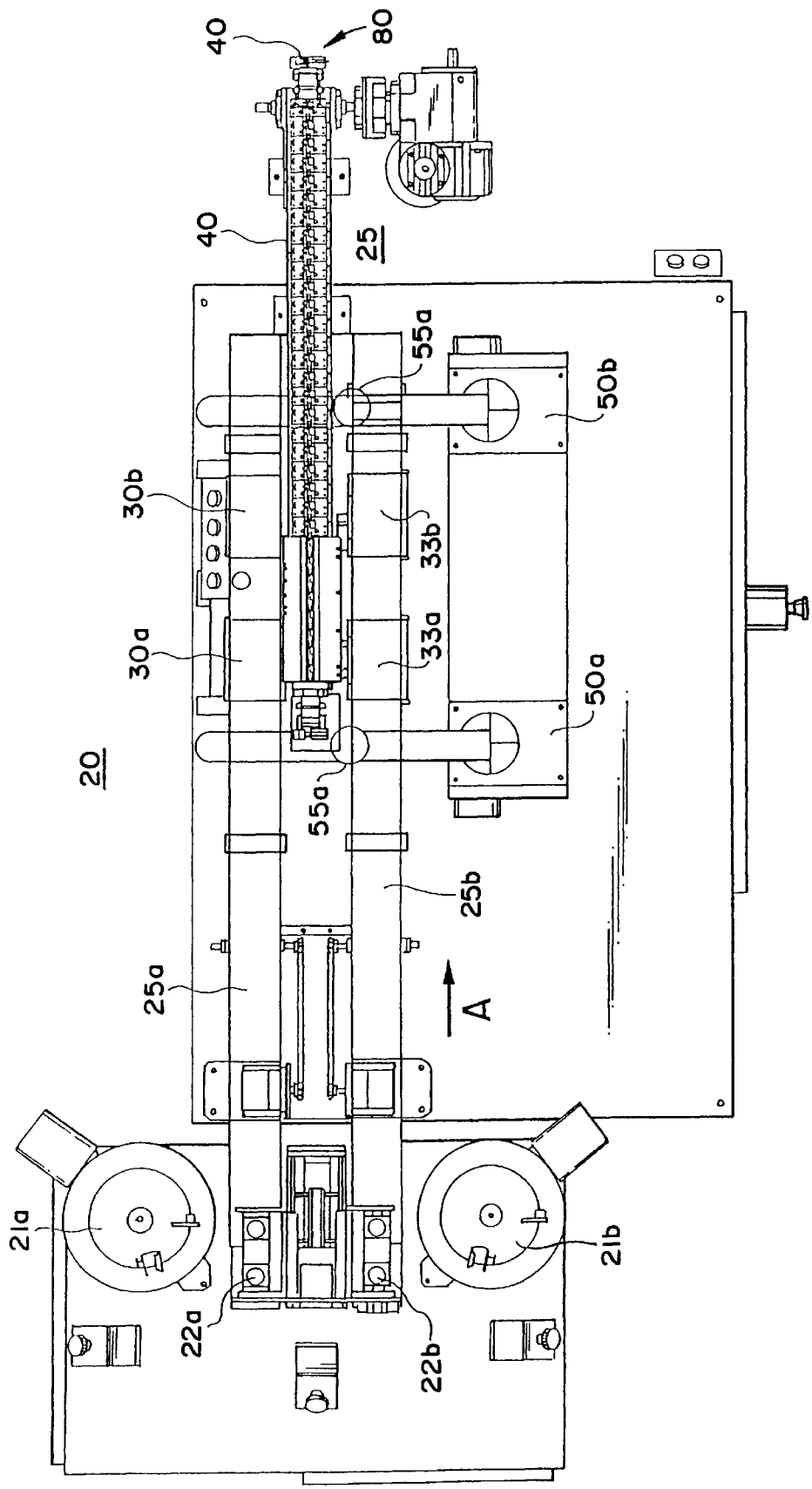
FIG. 3(a) is a top view of the needle sorting device 20 of the instant invention illustrating the initial vibratory bowl parts feeders which singulate the needles, the linear slide discharge mechanisms, the first and second translucent indexing conveyors, the robotic assemblies and the precision conveyor.
Figure 3B:
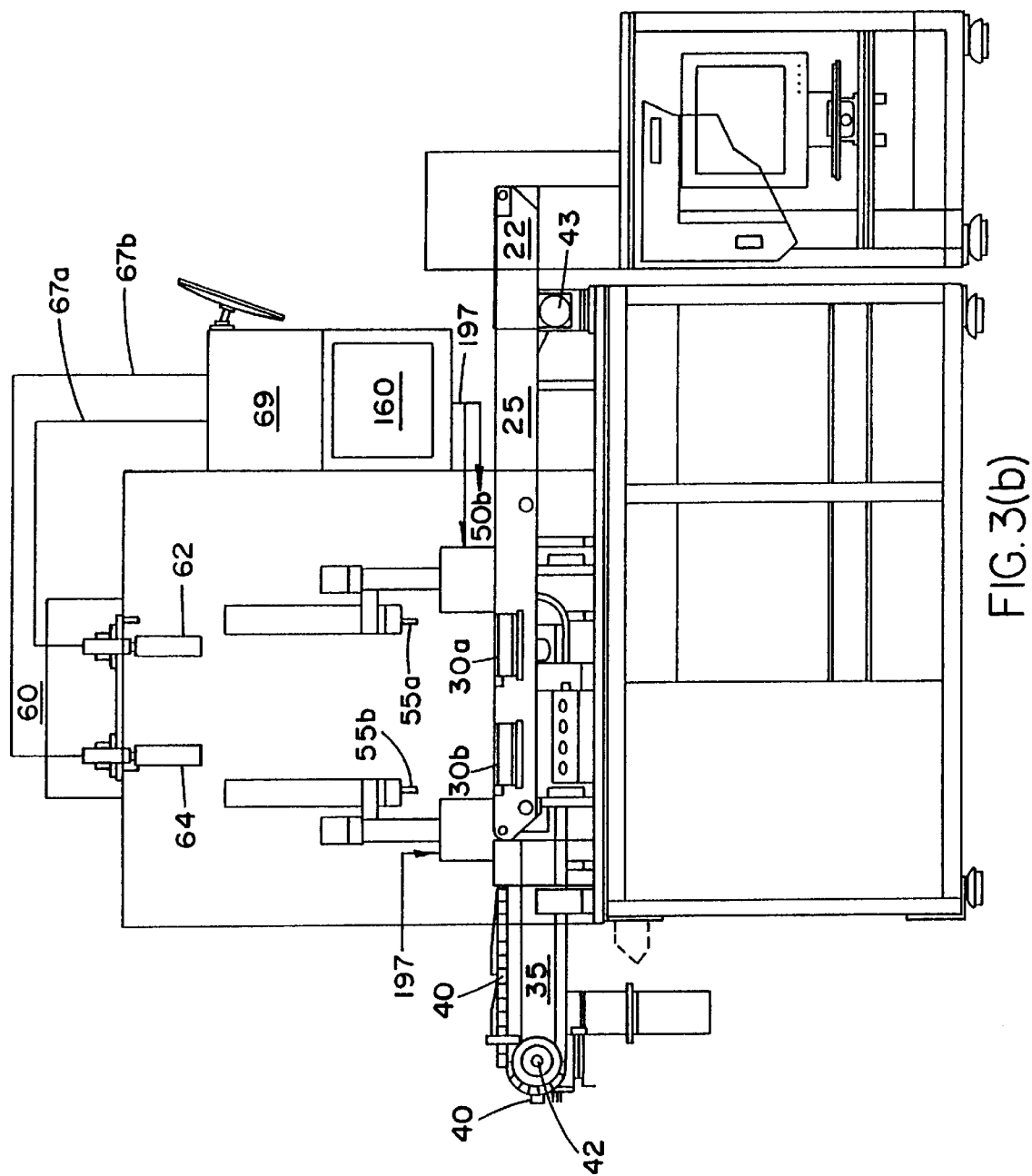
FIG. 3(b) is a side elevational view of the needle sorting device of FIG. 3(a) showing the robot assembly above the first conveyor means and the vision tracking means comprising two video cameras for obtaining images of the needles and the control system means for processing the image data.

The preferred embodiment of the needle sorting and infeed apparatus 20 is illustrated in the top view of the system in FIG. 3(a) and the side view of FIG. 3(b). As shown therein, needles 19 are delivered in bulk to each of two vibratory bowls or hoppers 21a,b where they are singulated by the vibratory bowls into a single file of needles, and intermittently fed to the linear slide discharge assemblies 22a,b where they are individually deposited upon each of two translucent conveyors 25a,b. The two translucent conveyors 25a,b carry the singulated and deposited needles 19 in the direction indicated by the arrow A in FIG. 3(a) where their position and orientation are evaluated by a remotely located vision tracking system that will be discussed in detail below with respect to FIG. 3(b).

The tracking system evaluates the position and orientation of each available needles on the translucent conveyors 25a,b as it forwardly conveys the needles over illuminated (backlit) platforms 30a and 33b and further evaluates the position and orientation of the each available needle upon translucent conveyor 25b as it forwardly conveys the needles over illuminated (backlit) platforms 33a and 33b.

The orientation and positional information obtained from the vision tracking system is processed and converted to coordinates usable by each of two robot assemblies 50a,b for instructing respective robot grippers 55a,b to pick up and transfer identified needles from one of the translucent conveyors to individual engagement boats 40, located on a precision conveyor 35 that is also being indexed in the same direction as the translucent conveyors as shown in FIG. 3(a).

The control system computer instructs a robot gripper, for e.g., gripper 55a of the robot assembly 50a, to grab the tracked needle from one of the two conveyors 25a,b for a dwell cycle of the system, i.e., when the respective conveyor has paused. If the singulated needles 19 are oriented such that neither of the robot grippers 55a,b are able to pick one of them up or place a needle onto the precision conveyor because of its limited range of motion, a recovery procedure will be executed to ensure that there are no shortages of needles 19 to be fed by the precision conveyor 35 to the automatic high-speed swaging workstation (not shown) which can achieve up to 60 needle swages per minute.

In the preferred embodiment, the timing of each conveyor 25a,b is identical, but the dwell periods are out of phase. Because of the phased timing, the vision tracking system will be identifying needles on one indexing conveyor, for e.g., 25a, while both robots are picking needles from the other indexing conveyor 25b and placing each needle in an individual engagement boat of the precision conveyor. Similarly, while both robots are picking needles from the indexing conveyor 25a, the vision tracking system will be identifying needles on the other indexing conveyor 25b.

The first step of the automatic swage/wind process 10 involves introducing a predetermined amount of needles 19 from an infeed device, such as a vibratory bowl or hopper, which serves as the first component in the needle singulating assembly.

This first step in singulating needles for the automatic swage/wind process 10 involves singulating individual needles from a bulk supply of needles for introduction to the vision inspection system. In the device illustrated and described in the parent application, U.S. Ser. No. 08/567,264 and U.S. Ser. No. 08/181,600, the singulating device separated needles into groups of three for deposit on a moving conveyor which needles were then imaged. Some of these needles fell in an overlapping relationship and when that happened, the vision system would automatically exclude that group of needles and the needles would then be recycled back to one of the vibratory bowls for a second singulation step. This recycling is undesirable inasmuch as it increases the risk that a needle point may become blunted by contact with other needles, or that the swage apparatus fed by the present invention may miss swage/wind cycles during operation.

The improvement of the present invention therefore includes an improved vibrating hopper assembly which singulates the needles into a single file, and a linear discharge slide mechanism which provides for timed and positioned placement of the needles on the translucent indexing conveyor.

As illustrated in FIG. 3A, a pair of vibrating bowls 21a and 21b are illustrated. In the preferred embodiment, both bowls 21a and 21b are provided with a singulating track for singulating the needles into single file, but only a single track is illustrated in FIG. 3A. A pair of linear slide discharge mechanisms 22a,b are also provided to transport and align individual needles from the vibrating bowls assembly 21a,b to the translucent conveyors 25a,b for imaging by the inspection system.

The function of the improved feed mechanism, including a vibrating bowl and a linear slide discharge mechanism, is to deposit individual needles in a spaced relationship on the translucent conveyor 25 for imaging by the vision system and subsequent handling by the robotic assemblies 50a,b.

Figure 4A:
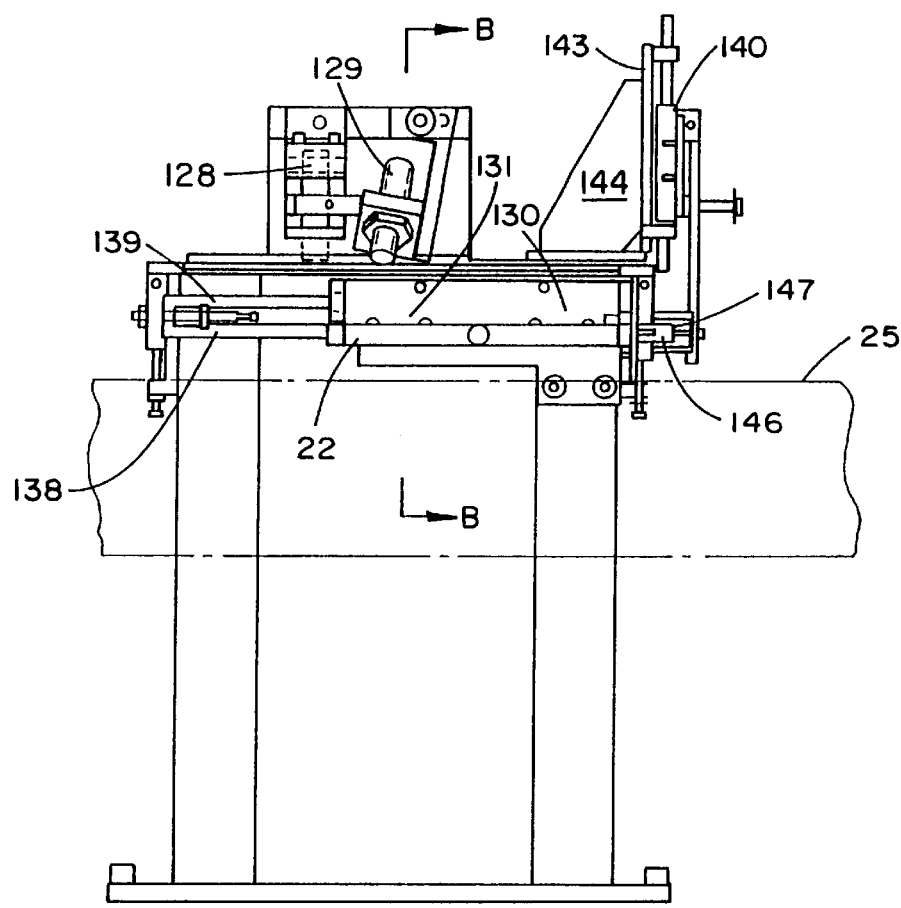
FIG. 4(a) is a detailed side elevation view of the linear slide mechanism used to singulate and deposit individual needles onto the translucent conveyors.
Figure 4B:
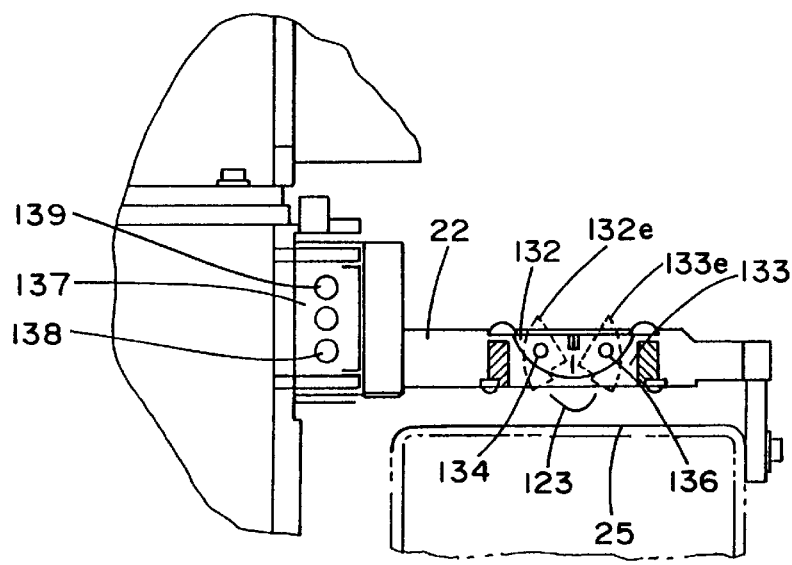
FIG. 4(b) is a detail cross-sectioned view of the linear slide device of FIG. 4(a) taken along section line B-B' showing the slide above one of the translucent conveyors.
Figure 4C:
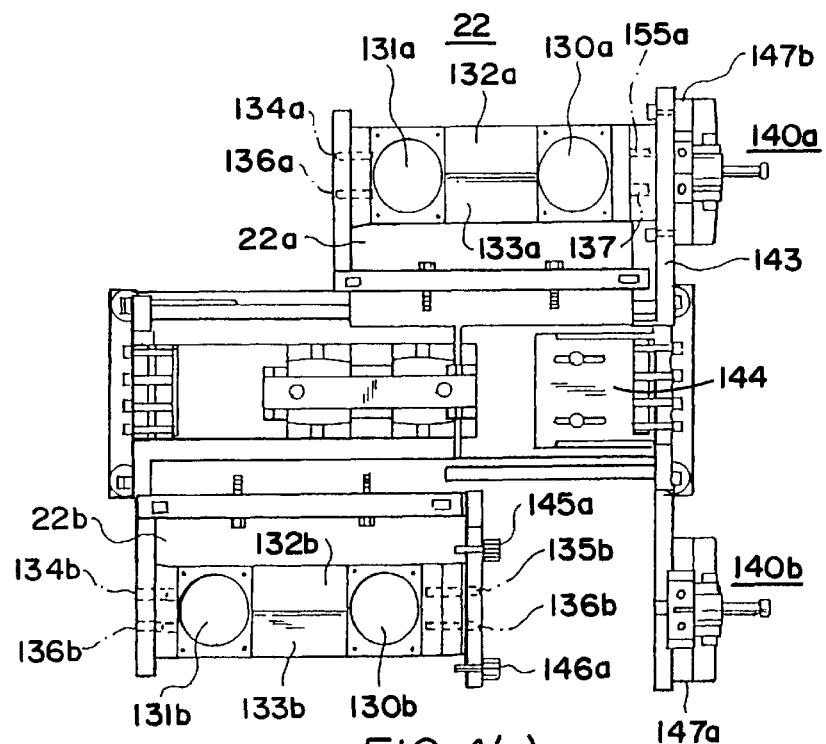
FIG. 4(c) is a detailed plan view of the linear slide mechanism illustrated in FIG. 4(a).

Two separate needle feed mechanisms are illustrated in FIG. 3(a) to feed two separate translucent indexing conveyors. In FIGS. 4(a)–4(c), the linear slide mechanisms 22a,b are illustrated in greater detail, and the vibrating bowl assembly is illustrated in greater detail in FIG. 4(d). Parts that are substantially identical in the two separate feed mechanisms are identified with the same reference numeral with an (a) or (b) suffix, depending on which feed mechanism they are associated with. When a part is referred to without the suffix, it is understood the description applies equally to both needle feed mechanisms.

Figure 4D:
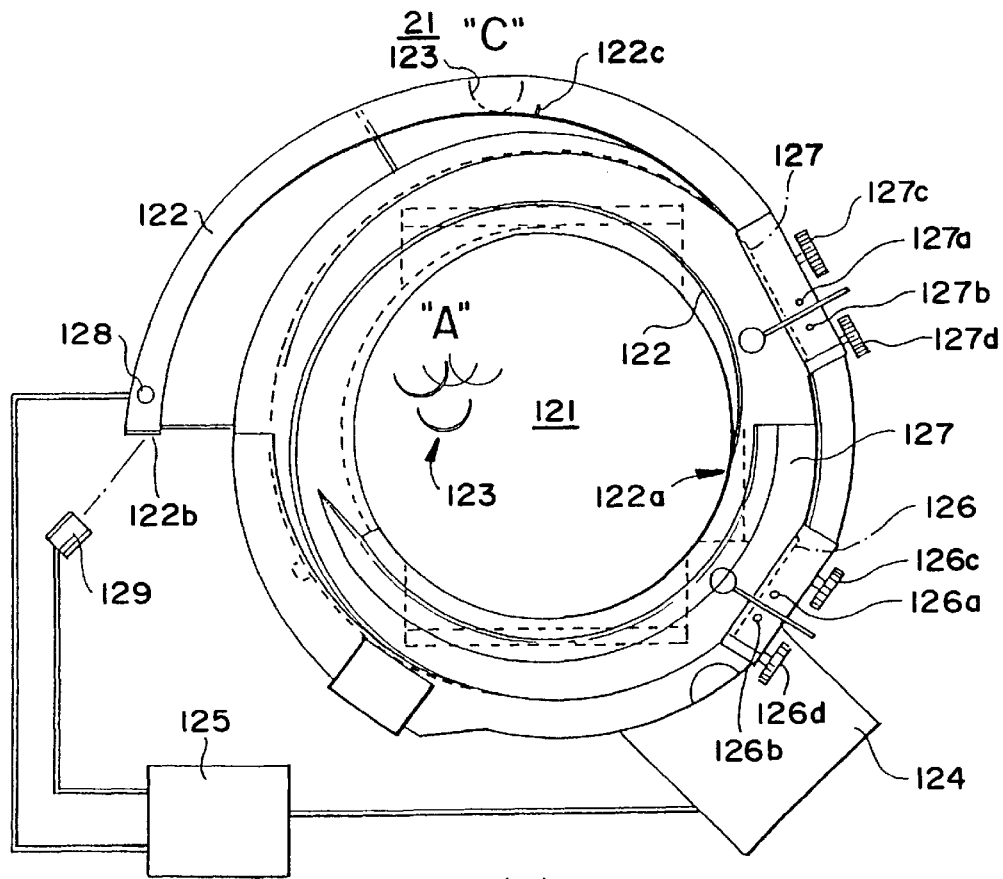
FIG. 4(d) is a detailed top plan view of one of the vibratory conveyor bowls and the needle trackway used to feed the linear slide mechanisms.

As illustrated in FIG. 4(d), a vibrating bowl assembly receives a plurality of needles in bulk on a central floor area 121. The vibrating bowl is a modified vibrating parts feed device manufactured by FMC Corp. to provide between 60 and 100 parts per minute. The bowl is fabricated of surgical stainless steel with a polyurethane lining in the bowl and all riding surfaces of the track assembly are also coated to prevent damage to the needle points. The track assembly 122 is a continuous spiral track which begins at the bottom of the bowl at 122(a) and ends at the linear discharge point 122(b). The track includes along virtually all of its entirety a vertical rib 122(c) which supports the needle during the vibratory transport as illustrated by the needle 123 at position C. The needles are transported from the floor 121 at position A to the discharge point 122(b) by pulsed vibration from vibratory unit 124 controlled by a control means 125. The vibrations supplied by the unit 124 are both vertical and horizontal and are timed to coincide to provide a maximum rate of movement for the needles 123. Track member 122 begins at the floor of the unit 121 and winds upwardly to the top of the vibrating bowl wherein the vertical portion 122c is interrupted for a pair of vertical gates 126 and 127 which redirect overlapping needles and nested needles back into the vibrating bowl 21. A secondary track and dam 127 is used to catch overlapping needles screened by the first dam 126 and return them to the floor of the hopper 21 with minimal damage to the points of the needle. Each of the vertical dams 126, 127 include adjustable knock off screws 126a,b and 127a,b which are used to provide precise adjustment of dams 126 and 127 for various needle sizes. Thumb screws 126c,d and 127c,d provide coarse adjustment of the gates 126,127 while knock off screws 126a,b and 127 a,b provide for fine adjustment thereof.

As stated earlier, the entire raceway track 122 and the vibrating bowl 21 are coated in polyurethane to minimize any damage to the needle points. The polyurethane coating on the stainless steel bowls and the silicone coating on the needles tend to create during operation of the device a static charge which can effectively inhibit movement of the needles along trackway 122. This static buildup may be countered in one of two ways, first by providing a stream of ionized air over the trackway or second by coating the polyurethane racetrack 122 with a Teflon spray lubricant available commercially. It has been found that an application of the Teflon spray lubricant will remain effective for approximately 500,000 needles.

The pulsed vibration of vibrating unit 124 provides a single file stream of needles oriented on trackway 122 as illustrated at position B and C by needles 123. As they reach the end of the track 122b, they are first detected by an optical sensor 128 which is activated by the reflection of the needle on the trackway 122. When the needle has fallen from the trackway at 122(b), a second detector signal is generated by a second optical detector 129. The electrical signals from optical detectors 128, 129 are provided to control means 125 for use in controlling the vibratory motor 124 as will be hereinafter described in greater detail.

Vibrating bowls 21a,b provide a serial single line output of needles, dispensed one at a time to the needle feed stations 22a,b which are more fully illustrated and described with respect to FIGS. 4(a)–4(c).

As illustrated in FIG. 4c, the needle feed stations include a first linear slide 22a and a second linear slide 22b which are reciprocated between the two positions illustrated in FIGS. 4(c) by slides 22a and 22b. In a first position, as illustrated by the linear discharge slide 22b, a first needle pocket 130 is arranged under the drop point 122b of the trackway 122a leading from the vibrating bowl members 121a,b. After sensor means 129 has detected a falling needle from the end of trackway 122, the linear slide is reciprocated to its second position illustrated by slide 122a in FIG. 4c. In this position, the second needle cup 131a is now positioned below the end of a trackway 122b formed on the vibrator bowl assembly 21a. The pulsing vibrator unit 124 is then energized until a second needle is detected by optical sensor 129 as it falls into needle pocket 131a.

The needle pockets 130 and 131 are formed in a pair of pivoting blocks 132,133 which are mounted for pivotal movement on the slide mechanism 22a,b. As illustrated in FIG. 4(c), block member 132a pivots on pins 134,135 while block member 133 pivots on pins 136, 137.

The pivotal movement is illustrated in FIG. 4(b) wherein block members 132, 133 pivot around pivot points 134,136 to the position illustrated at 132(e) and 133(e). As the block members 132,133 pivot, the needle pockets are opened as illustrated in FIG. 4(b) to deposit the needle 123 on the translucent indexing conveyor 25. An air slide mechanism 137 and guide rails 138, 139 which provide the reciprocal movement of the slide mechanisms 22a,b are also illustrated in cross-section in FIG. 4(b).

Referring to FIG. 4(c), the block members 132, 133 are pivoted by means of a second pair of air slides 140a,b which are mounted on a vertical plate 143 which is suspended above translucent conveyors 25a,b by means of a support base 144. Each of the blocks 132,133 is also equipped with rollers 145, 146 which engage a rectangular raceway 147 when the linear slide mechanism is reciprocated to its forward position as illustrated by slide 22a in FIG. 4(c). When the rollers 145(b),146(b) are received within rectangular raceway 147(b) the air slide 140b is actuated to raise the rectangular raceway 147(b) vertically. Since block members 132, 133 are mounted for pivotal movement with pins 134, 136 on the inbound side of the blocks, a lifting motion on the rollers 145, 146 on the outbound side of the blocks will cause pivotal movement about pins 134,136 as the rollers 145, 146 come together withing the rectangular raceway 147. After the needles have been deposited on the translucent conveyor 25, the air slide 140 is then lowered which returns block members 132, 133 to the position illustrated in FIG. 4(c).

In the sequence of operation, the control means 125 energizes the vibratory motor 124 to vibrate the bowl in a pulsed manner, with the amplitude of the pulses controlled by an adjustable rheostat. The adjustable amplitude setting varies depending upon the size and mass of the needle to be transported along the trackway 122. The needles are then singulated in single file along the entire length of the track 122 from the floor of the vibratory bowl 121 to the discharge point 122b. When optical sensor 128 senses the presence of a needle at the end of the trackway, vibrating motor 124 is stopped until the reciprocating slide 122 is reciprocated to its most rearward position as illustrated in by slide 22b in FIG. 4(c). After linear slide 22b is in position, control means 125 energizes the motor 124 and the needle is vibrated from trackway 122 into needle pocket 130b. As the needle falls from the trackway to the pocket, its presence is detected by optical sensor 129. Control circuit 125 keeps motor 124 vibrating until another needle is sensed on track 122 by sensor 128. After receiving a needle, the linear slide 22b is then advanced to the forward position as illustrated by slide 22a in FIG. 4(c). In the event a second needle is detected by optical detector 128 before slide member 22b has reached its forward position, the drive motor 124 is stopped until slide member 22b is in position to receive the second needle. Thus there are two control situations for the deposit of a needle into the second pocket 131b. If a needle was detected at sensor 128, then the vibrating motor 124 is reenergized to vibrate that needle off the end of track 122 and into needle pocket 131b. If a needle has not been detected by optical sensor 128, the control means will keep vibrator 124 running following the first drop, and the vibrator will continue to run until sensor 129 detects a dropping needle. After each drop, the control means 125 keeps the vibrating motor 124 running until a needle is detected at optical sensor 128. After both needle pockets 130b, 131b have received a single needle, the air slide 141 is actuated opening the needle cups and depositing the needles therein in a singulated and spaced relationship on the translucent conveyor 25 for imaging by the optical system and further handling by the robotic tracking system.

It should be understood that while the needles 19 deposited on translucent conveyor 25a,b are singulated and spaced apart, they will be randomly positioned and unoriented. In the preferred embodiment, each translucent conveyor 25a,b is an endless loop conveyor that is driven at a rate of four inches per sec (4 in./sec) and runs parallel to a precision conveyor 35 as shown in FIGS. 3(a).

As described above, and in view of FIG. 3(a), the robot assembly comprises two robots 50a,b located downstream from each needle singulating assembly 22a,b and proximate both the precision and translucent indexing conveyors. In the preferred embodiment described herein, each robot assembly 50a,b is an Adept® 604-S robot capable of accomplishing needle transfers at a rate of approximately 40 transfers per minute as controlled by each robot's corresponding Adept® CC controller. Each robot is a four-axis SCARA (Selective Compliance Assembly Robot Arm) robot comprising four Joints: Joint 1, being the shoulder joint having a rotational range of motion of ±100°; Joint 2, the elbow joint, having a rotational range of motion of ±140°; Joint 3 providing translational motion for a robot quill for up to 150 mm in an up down motion; and, Joint 4, being the wrist joint, providing ±360° rotational motion of the quill. Robot grippers 55a,b are attached to the quill of each respective robot assembly 50a,b and are enabled to provide gripping action by pressure supplied from an air cylinder (not shown).

Referring now to FIG. 3(b), there is illustrated the precision conveyor 35 which is driven by drive motor assembly 42 at a rate sufficient to index and transfer one oriented surgical needle per second (1 needle/sec) to the automatic swaging machine. A similar drive motor assembly 43 is provided for driving the indexing conveyors 25a,b. As will be explained in detail below, each drive motor assembly 42,43 is interfaced with and operates under the control of the control system 69 to pause the indexing motion to enable the pick-up and transfer of a needle from the indexing conveyor to the precision conveyor.

Figure 5:
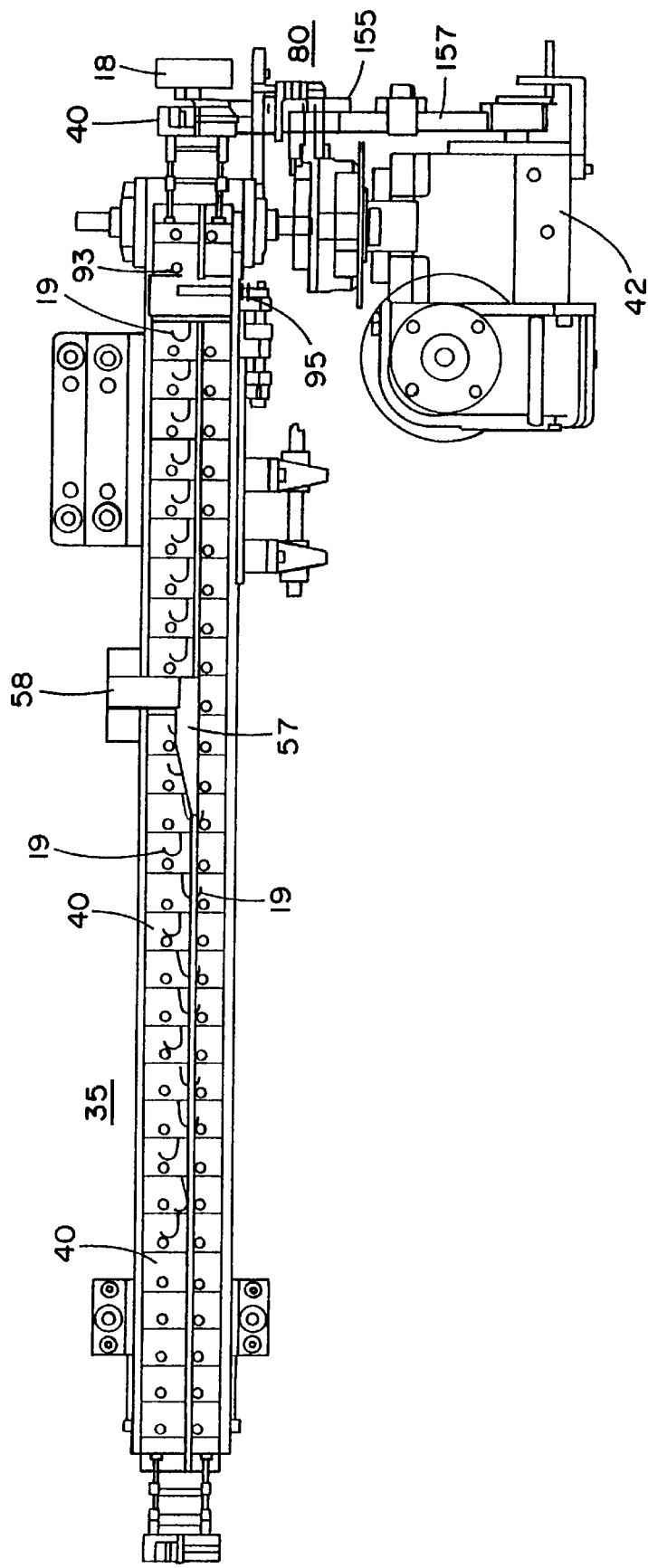
FIG. 5 is a top view of the precision conveyor and illustrates the conveyor, the needle plow mechanism, the needle pre-positioning mechanism, the moveable hard stop and the multi-axis gripper. The conveyor is shown carrying needles that have been positioned thereon.
Figure 6A:
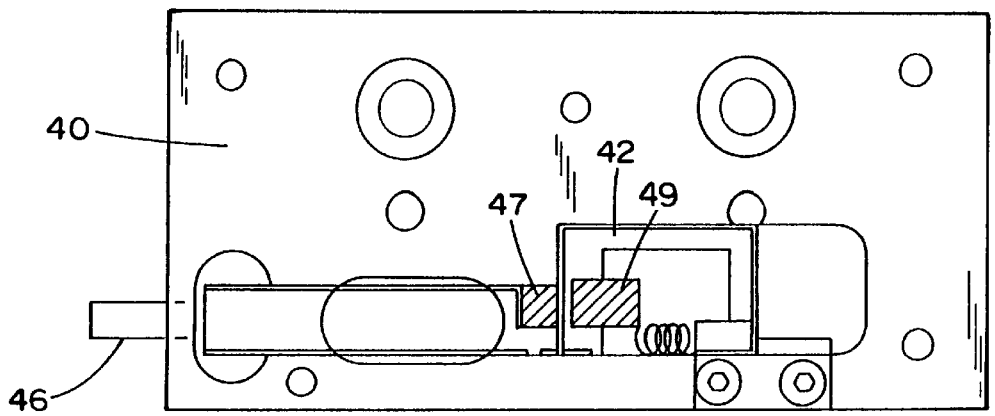
FIG. 6(a) is a detailed view of the precision conveyor boat having jaws for engaging and retaining an oriented needle for subsequent swaging.
Figure 6B:
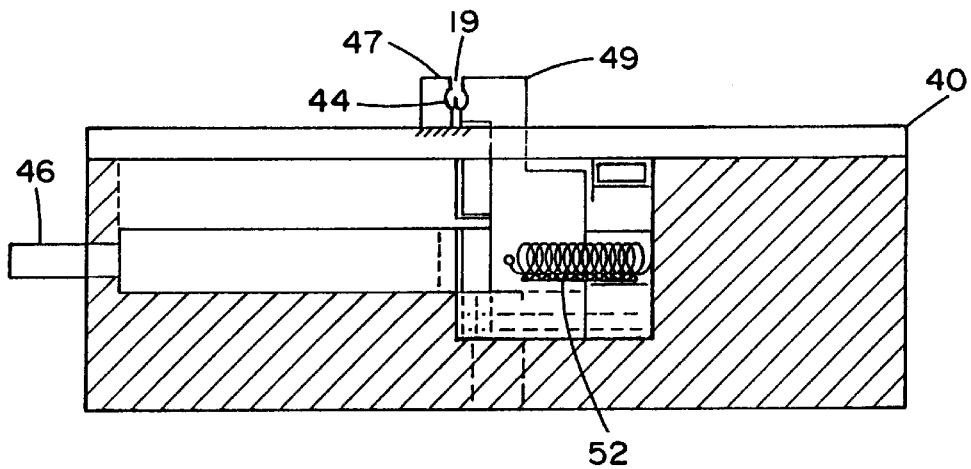
FIG. 6(b) is a detailed elevation view of the precision conveyor boat taken along line 5—5 of the boat illustrated in FIG. 5(a).
Figure 6C:
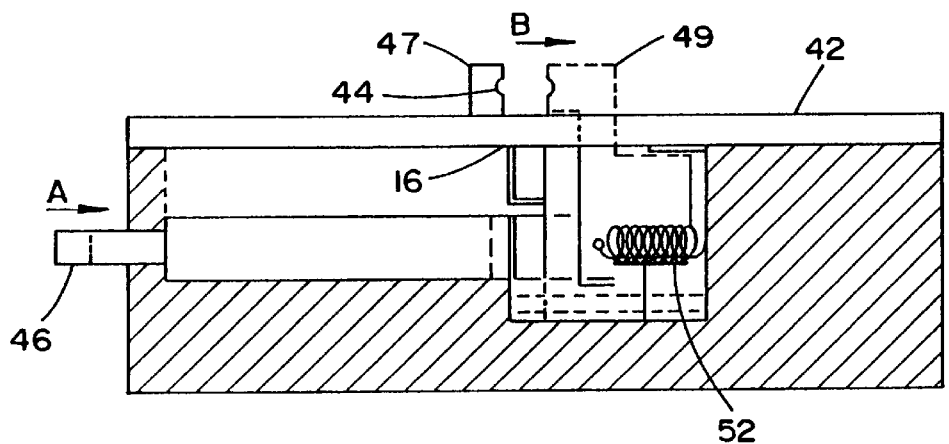
FIG. 6(c) is a detailed view of the precision conveyor boat with movable jaw extended for placement of needle oriented for automatic swaging.

FIG. 5 illustrates in detail the precision conveyor 35 and the plurality of engagement boats 40 located thereon for engaging respective individual surgical needles 19. Motion of the precision conveyor 35 is also paused periodically at the desired cycle rate to allow for the transfer of the needles 19 thereto from the robots 50a,b. The precision conveyor receives needles 19 with rough positioning from the robotic assemblies 50a,b, in boats 40 as will hereinafter be described in greater detail with respect to FIGS. 6(a)–(c) and 7. The needles when received in boats 40 are orientated as to point and butt end, but not orientated with respect to the direction of curvature of the needles. As further described with respect to FIGS. 9(a)–(e), a needle plow mechanism 57 is provided to orient the curvature of the needles. A needle pre-positioner 95 is also provided to provide prepositioning of the butt end of each needle as will be hereinafter described with respect to FIGS. 10(a) and 10(b). The needles are finally precisely positioned by the moveable hard stop mechanism 80 and will described in greater detail in FIGS. 11(a) and 11(b). The individual needles are then removed and held for swaging to a suture by a multi-axis gripper 18, which gripper is described in greater detail in FIGS. 14(a) –(c).

In the preferred embodiment, the control system 69 includes a programmable logic controller (PLC) that is in digital communication with the Adept® robot controllers and the vision tracking system components to control the infeed system.

As shown in FIG. 3(b), the vision tracking system comprises a camera assembly 60 having two video cameras 62 and 64, one located overhead each respective illuminated platform portion, 30a and 30b, for its indexing conveyor 25a. As will be explained in detail below, the video images of the needles obtained from each camera 62,64 are bit-mapped or suitably digitized and transmitted via suitable transmission media, such as communication lines 67a,b shown in FIG. 3(b), to the remotely located control system computer 69 where a Vision Control task processes the video images and inputs the data to each robot 50a,b via communication line 197. Preferably, the conveyors 25a and 25b are translucent and are backlit at the respective portions 30a,b and 33a,b so that a sharp video image may be obtained by the overhead camera assembly for processing.

It is understood that for descriptive purposes, only two video cameras 62,64 corresponding to the two illuminated platforms 30a, 30b are shown in FIG. 3(b). However, the invention includes a second set of video cameras (not shown) corresponding to illuminated platforms 33a and 33b for conveyor 25b so that, as mentioned above, binary images of needles on conveyor 25b may be obtained while the robots are picking and placing needles from conveyor 25a. The redundancy designed into this system ensures that there will be no momentary shortage of needles fed to the swaging station and that maximum throughput of oriented needles for input to the swaging station is achieved.

In the event the state of robotics technology improves, and as the robot assemblies achieve greater degrees of movement at faster speeds, the second set of cameras and a second robot assembly may no longer be required. Furthermore, a robotic assembly of sufficient speed and precision may be able to pick up randomly deposited needles from a moving conveyor and place them directly in an oriented position at the swaging station.

In the preferred embodiment, each camera 62,64 is mounted approximately one (1) meter above each backlit indexing conveyor 25a,b and utilizes an electrically controlled telephoto lens with a focal distance ranging from 10 mm to 140 mm that may be changed with suitable adaptors. Suitable lens controllers are used to establish lighting/iris, focus, and field of view for each camera lens, and, are interfaced with the Adept® controller via an RS-232 link.

A further component of the control system for the needle sorting and infeed apparatus includes an SCADA Node which is used to oversee and direct the infeed system. This node interfaces with each of the Adept® controllers via discrete RS-232 links which are used to download data information, such as needle parameters, error messages, and status messages, to the Adept® controllers during run-time. The SCADA node may comprise a personal computer or such suitable device, running commercially available FIXD-MACS® software. Serial communication is used to exchange the needle parameters entered at the FIX/DMACS "Adept® Setup" screen during a needle changeover procedure which is used to inform the infeed system of the size and type of needles to be processed. After an operator enters the needle parameters and initiates a changeover, the FIX/DMACS Node will transmit these parameters to the robot controller(s).

Figure 8:
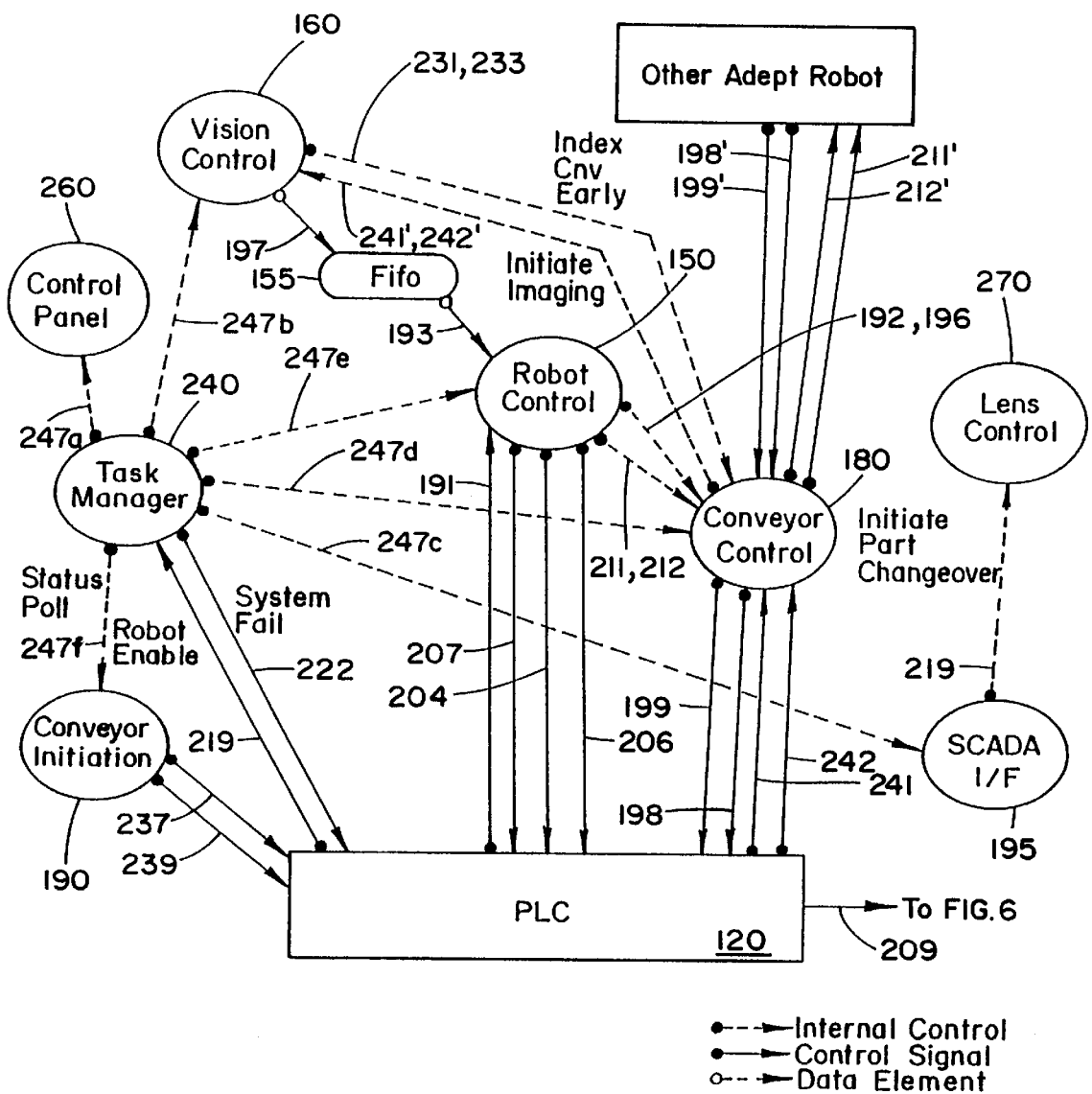
FIG. 8 is schematic representation of the control and data flow for each of the control tasks of the needle sorting apparatus of the present invention.

The robotic/vision control system 69 of the invention comprises individual computer software programs, each associated with a particular task to be performed by the needle sorting and infeed system 10 and executed under the control of the PLC 120. As shown in FIG. 8, the software architecture for controlling the needle sorting apparatus of the instant invention performs eight (8) main tasks: a Robot Control task 150; a Vision Control task 160; a Conveyor Indexing Control task 180; a SCADA Node Interface task 195; A Control Panel task 260; a Task Manager 240; a Conveyor Initiation task 190; and, a Lens Control task 270. Of these eight tasks mentioned above, the first six are active during the needle infeed steady state operation as will be explained below. FIG. 8 additionally shows the data flow among the tasks and the signals which initiate the tasks. It is understood that the software language used in the preferred embodiment, is Adept's V/V+ language, which supports both vision and robotic control in a multitasking environment. Each of the tasks will be generally described below with respect to FIG. 8. A more detailed description of the following tasks can be found in the above-mentioned U.S. Pat. No. 5,568,593.

It should be understood to those skilled in the art that each robot assembly, controllers, and camera vision tracking system requires careful calibration and configuration procedures for the infeed system to properly function. For instance, each robot assembly requires that joint positions be set and joint limits be configured to ensure that the robots avoid structural damage when enabled. Furthermore, a camera-to-robot calibration is required so that the vision system may accurately compute the positional coordinates of the needle so that the robot may move to the pick position. This procedure provides a translation matrix between the camera's field-of-view and each robot base position.

The PLC 120 is responsible for initially powering the robot controllers and robots. A robot calibration procedure may be initiated after power-up to move the robot joints to known "home" positions to synchronize the digital encoders (not shown).

The process of starting the PLC 120, robot controllers, and conveyors 25a,b and 35 is time-critical. From the robot controller perspective, when a ROBOT ENABLE signal 219 is raised by PLC 120, it begins its normal cycle by executing the Robot Control Task 150, the Vision Control Task 160, the Conveyor Indexing Control Task 180, and the Conveyor Initiation Task 190; which initiates the movement of conveyor 25a, waits approximately up to two (2) seconds, and then initiates the movement of second conveyor 25b as will be described in detail below. The PLC simultaneously raises the ROBOT ENABLE signal on the other Adept robot. Under this scenario, the PLC integrates the startup of the Bulk Feeding Device System, the Indexing Conveyors, and swaging machine with the raising of the ROBOT ENABLE signal 219. As will be explained in further detail below, when the ROBOT ENABLE signal goes low, the Adept robot halts its standard processing and responds to requests from the SCADA node.

Robot Control Task

There is a single Robot Control task associated with each Adept® controller for each robot assembly 50a,b although only one is indicated as element 150 in FIG. 8. The control system software for the Robot Control task 150 manages the respective robot assembly 50a or 50b as a resource, reads a FIFO buffer 155 of identified needle locations which are produced by and input from the Vision Control Task 160, interfaces with the programmable logic controller (PLC) 120 of control system 69 for needle placement handshaking, and, initiates the indexing of the conveyor belts 25a,b.

The steady state operation of the Robot Control task 150 for each robot assembly 50a, (50b) is as follows:

First, the respective robot controller continuously polls its input FIFO 155 via data line 193 to obtain positional coordinate data for the identified needle locations on a respective translucent conveyor 25a or 25b. The data for the needle locations are provided to the FIFO buffer from the Vision Control task 160 via respective data lines 197 as will be explained in further detail below. When an acceptable (recognizable) needle position is entered into the FIFO buffer 155, the robot controller will remove the needle position from the buffer and direct the robot gripper arm 55a,(55b) to move to that location on the conveyor belt. Next, for each recognized needle, the Robot Control task 150 will signal the robot gripper 55a,(55b) to close on the needle barrel portion 7 and to depart from the conveyor to an approach location proximate the precision conveyor 35. The robot control task then generates a NEEDLE IN GRIPPER signal 207 to the PLC as indicated and waits for a response from the PLC 120. As shown in FIG. 8, when the PLC receives a Robot task generated NEEDLE IN GRIPPER signal 207, the PLC 120 will generate a SAFE TO PLACE signal 191 for receipt by each of the robots 50a,b. The purpose of the SAFE TO PLACE signal 191 is to inform the respective robot assembly 50a,b that a needle may be placed onto a precision conveyor boat 40 of conveyor 35. As a response to the receipt of the SAFE TO PLACE signal 191, the Robot Control task 150 will generate a DON'T INDEX PRECISION CONVEYOR signal 204 for receipt by the PLC 120 immediately before it places the needle on the precision conveyor 35. While this signal remains high, for e.g., at a logic "1" state, the Adept® robot 50a or 50b will attempt to place a needle onto a boat 40 of precision conveyor 35. This involves initiating the engagement jaws 47,49 of the precision conveyor engagement boat 40 to retract to allow the placement of the needle therebetween, as will be explained below. Once the movement of the robot has settled and a needle is placed, the Robot task 150 will generate a NEEDLE PLACE COMPLETE signal 206 for receipt by the PLC 120 and, the PLC will generate a suitable control signal 209 to enable the engagement jaws of the precision conveyor engagement boat 40 to engage the needle. In the preferred embodiment, the dwell time of the NEEDLE PLACE COMPLETE signal 206 is approximately 48–64 milliseconds. After activating this signal, the robot assembly 50a,b will hold the needle in place for the same time period. (48–64 msec.) Immediately thereafter, the robot will open its grippers and move back to its approach location away from the engagement boat 40. Finally, the DON'T INDEX PRECISION CONVEYOR signal 204 is removed indicating that it is now clear for the precision conveyor 35 to index which is performed at the command of the PLC 120.

As a safety interlock for conveyor index initiation, the Robot Control Task 150 will signal the Conveyor Indexing Control Task 180 with an internal control respective LAST PICK signal 192, 196 indicating that the robot assembly, 50a or 50b, has picked up the last needle from the current conveyor as indicated in FIG. 8. If the maximum number of needles expected per current camera field-of-view (hereinafter "FOV") is not picked from the respective current infeed conveyor belt 25a,(b), the Robot Control Task 150 will request the Conveyor Control task 180 to index that conveyor belt "early" via the INDEX CONVEYOR 1 EARLY or the INDEX CONVEYOR 2 EARLY signals 211,212 as shown in FIG. 8. Since all signals affecting the motion of the conveyors are routed through the Conveyor Control task 180, this task will generate a corresponding INDEX CONVEYOR 1 EARLY, signal 211' INDEX CONVEYOR 2 EARLY, signal 212', for receipt by the other adept robot. If during normal operation a Robot Control Task receives either Index Conveyor 1 Early or the Index Conveyor 2 Early signal, it will flush the contents of its FIFO buffer 155 and continue as if the last needle has been picked from the conveyor.

The control software must take into account the floating 16–32 ms duration of a digital output based on the time slicing of V/V+. This will affect the calculation for minimum time required for placement in conjunction with setting and resetting the Don't Index Precision conveyor signal 204.

The Robot Control Task 150 performs error recovery on two type of errors. These errors are grouped as indexing errors and gross errors. As in all other tasks, gross errors cause the Task Manager 240 error recovery to respond and stop the Robot Control Task immediately. An indexing error occurs if a robot is waiting for a needle to be placed in its parts FIFO and both conveyor belts have not indexed within an appropriate amount of time. The Robot Control Task 150 recovers from this type of error by requesting the other robot to index early via signals INDEX CONVEYOR 1 EARLY and INDEX CONVEYOR 2 EARLY signals 211,212 respectively. This forces both vision/robot control systems to flush the contents of its current parts FIFO and index the conveyor belts.

Conveyor Indexing Control Task

The Conveyor Indexing Control Task 180 initiates the indexing of each respective translucent indexing conveyor 25a,b and the task is initiated by the Conveyor Initiation task 190. All signals affecting the motion of the conveyors are routed through the Conveyor Control task 180.

As shown in FIG. 8, the first step of the Conveyor Indexing Control task 180 is to check for the LAST PICK signal 192,196 internally generated from the Robot Control Task 150 and indicating that the last needle pick-up from the respective infeed translucent conveyor 25a,25b has been completed by one of the Adept® robots 50a,b. Alternatively, the Conveyor Indexing Control task 180 awaits for the INDEX CONVEYOR EARLY (1 and 2) signals 231,232 internally generated from the Vision Control task 160 when no needles are recognized in the current camera FOV. As a result of receiving the LAST PICK signals 192,196 from the robot task, the Conveyor Control task will generate a corresponding INDEX CONVEYOR 1 signal 198, or, an INDEX CONVEYOR 2 signal 199, for receipt by the PLC 120. It is understood that each Adept® robot controller must request the PLC 120 to index a translucent indexing conveyor 25a(,b) after picking up the last needle from the respective conveyor. Therefor, the other Adept® robot must generate its corresponding INDEX CONVEYOR 1 (or INDEX CONVEYOR 2) signal for receipt by the PLC before it can command the current translucent conveyor 25a,(25b) to index. As a result of receiving the INDEX CONVEYOR 1 EARLY, signal 211' or INDEX CONVEYOR 2 EARLY, signal 213' from the Conveyor Control task 180 indicating that the maximum number of needles have not been picked up or that there are no or insufficient needles in the respective camera's FOV, the other Adept robot will generate a corresponding CONVEYOR 1 INDEXED EARLY signal 198', or CONVEYOR 2 INDEXED EARLY signal 199' for receipt by the Conveyor Control task 180, as shown in FIG. 8. These signals will cause the corresponding conveyor 25a(,b) to abort processing and initiate indexing of the belt.

After receipt of both INDEX CONVEYOR 1 or INDEX CONVEYOR 2 signals 198,199 from each of the robot assemblies, the PLC 120 commands the translucent indexing conveyor 25a to index and generates a corresponding CONVEYOR 1 SETTLED signal 241 or, a CONVEYOR 2 SETTLED signal 242 for receipt by the Conveyor Control Task 180. Note that the CONVEYOR 1 SETTLED signal 241 and the CONVEYOR 2 SETTLED signal 242 are raised approximately 2 seconds after the PLC has been requested by the robot control task 150 to index conveyor 25a, (25b). The Conveyor Control Task 180 then informs the Vision Control task 160 to begin needle imaging upon receipt of internal control signals 241',242' that correspond to the respective CONVEYOR 1 SETTLED and the CONVEYOR 2 SETTLED signals 241,242. Once the indexing conveyor 25a (25b) has been indexed and the corresponding CONVEYOR SETTLED signal 241,242 has been received, the Vision Control Task 160 may begin needle recognition in the corresponding cameras's FOV. Specifically, as will be explained below, the cameras 62,64 above conveyor 25*a,b* each take a snapshot of the respective field of views at respective illuminated portions 30*a,b* of the translucent conveyor and the Vision Control task 160 will control the processing of the image to make a determination of whether a recognizable needle is present each camera's field of view.

At this point, a distinction must be made between the mere presence or detection of a needle in the field of view and the presence of a "recognizable" needle. A needle may be present, but, for a variety of reasons, the Vision Task 160 may not be able to determine its positional coordinates until the camera vision parameters are changed by the execution of an auto-imaging algorithm which automatically adjusts the iris and vision system lighting parameters of each camera so that the cameras may subsequently obtain enhanced images that may be processed. During steady state, when the vision task has already "recognized" a needle in its respective field of view, the auto-imaging algorithm is not repeated.

Details of the auto-imaging algorithm will be explained in detail below.

Vision Control Task

The Vision Control Task 160 controls and processes the images taken by each of the two camera assemblies 62,64. Since the timing of the two translucent conveyors are phased, only one camera is operating at one time.

Specifically, as shown in FIG. 3(*b*), the Vision Control task 160 interfaces with each respective camera 62,64 to identify the needle locations of recognizable needles in that camera lens's respective field of view encompassing an area located at respective illuminated platforms 30*a*,30*b*. The Vision Task 160 then processes the positional and orientation information of the identified needle locations and writes those locations to the Robot Task FIFO 155 via data lines 197. As mentioned above, the Vision Control task is additionally responsible for initiating an early conveyor index if no needles were imaged in a camera field of view.

As described briefly above, the Vision Control task runs each time either conveyor 25*a*,25*b* completes indexing. It is initiated to begin needle recognition upon receipt of either a CONVEYOR 1 SETTLED signal 241' or CONVEYOR 2 SETTLED signal 242' which is generated by the PLC 120 and routed through the Conveyor Control task 180 each time respective translucent indexing conveyor 25*a*,25*b* has ceased indexing, as commanded by the Adept®. Each CONVEYOR SETTLED signal 241,242 goes high (logic "1") approximately two (2) seconds after the PLC has been requested by the Adept® robot to index a translucent indexing conveyor. Each of the CONVEYOR SETTLED signals 1 and 2 (241,242) remain high until the PLC 120 receives the next respective INDEX CONVEYOR 1 or 2 signal 198,199 from the Adept robots.

The Vision Task 160 activates that camera which is associated with the conveyor settled signal. When activated, the camera 62,64 takes a picture of the backlit areas 30*a,b* of the conveyor belt 25*a*,(25*b*). Any image obtained is preferably converted to binary image data for subsequent digital processing. The Vision Control task 160 utilizes "vision tools" to detect acceptable needles, and places the coordinates of acceptable needle pick-up points in the FIFO buffer 155 for the Robot task. An "acceptable" needle in the backlit areas is a needle that measures within the tolerances of the needle parameters that have been previously accepted during the needle changeover procedure. The needle changeover procedure is a procedure to inform the infeed system software of the type and size of the needles in the current batch to be processed and must be executed before making needle batch changes as to be discussed below. Specified needle tolerances are for the needle radius, barrel width, angular characteristics of the needle with respect to the robots, and the calculated area as computed from the needle parameters.

Auto-Imaging Algorithm

As mentioned above, if a detected needle is unrecognizable, the auto-imaging algorithm is invoked to change the camera vision parameters. Thus, after the binary image data is processed, a determination is made as to whether the needle image is of the specified radius, whether the needle image is of the specified barrel width, whether the needle image has the specified angular characteristics, and, whether the needle image area is within the specified tolerance. If any of these criteria are out of specification, then an auto-imaging algorithm is executed which functions to take a series of pictures of the same needle image at the respective camera's field of view to thereby enhance the needle image for better needle recognition by improving the vision parameters between pictures. Thus, after each of the series of pictures is taken, the auto-imaging algorithm will automatically adjust the camera's iris and vision system lighting parameters to enable the vision system to image the needles properly within the camera's field of view. For example, when adjusting the lighting of the fields of view, certain camera vision parameters such as the gain, offset, and binary threshold may be modified. The auto-imaging algorithm is executed until a needle is recognized in each camera's field of view and is not repeated until a needle changeover is executed.

Even when the cameras of the Vision Control task 160 are adjusted, needle images may still not be imaged properly. This is because each camera's field of view utilizes a backlighting source and needles that overlap, touch with each other, or, are clipped by field of view edge boundaries will not be considered for recognition. Thus, the Vision Control task will make a determination of whether the needles overlap or touch each other, and, will determine whether the needles are too close to the edge of the field of view.

After all of the possible needles are recognized, the Vision Control task will calculate the needle pick-up coordinates of the acceptable needles and place them in the Robot Control task FIFO buffer 155 to enable the robot to pick and place the acceptable needle onto the precision conveyor. In the preferred embodiment, the maximum number of needles that can be recognized during each dwell cycle of each translucent indexing conveyor is three (3). If less than this maximum or if no needles are recognized, a robot may be signaled to index the corresponding conveyor early, causing the vision system to abort its processing as described above.

Vision Task 160 is responsible for limiting the number of needle locations written to the FIFO to three, since the Robot Control Task will pick and place a needle for every needle location passed to the FIFO 155. In the preferred embodiment, the Vision Task is limited to operate for five seconds per indexing conveyor cycle.

The Vision Control Task 160 performs error recovery on three types of errors. These errors are grouped as imaging errors, processing errors, and gross errors. The gross errors cause the Task Manager error recovery to respond and stops the Vision Control Task 160 immediately. When an imaging error occurs, the Vision Control Task 160 suspends all execution on the current FOV and requests an early index of the conveyor belt by generating either INDEX CONVEYOR 1 EARLY or INDEX CONVEYOR 2 EARLY signals 231, 233 as discussed above. Receipt of these signals causes no needles to be placed in the parts FIFO and forces both vision/robot systems to pass on the current FOV of needles. If a processing error occurs, the Vision Control Task suspends all processing on the current needle and begins processing a new needle in the same FOV if another needle is available. As a result, the Vision Task does not insert the needle into the parts FIFO.

Conveyor Initiation Task

Figure 7:
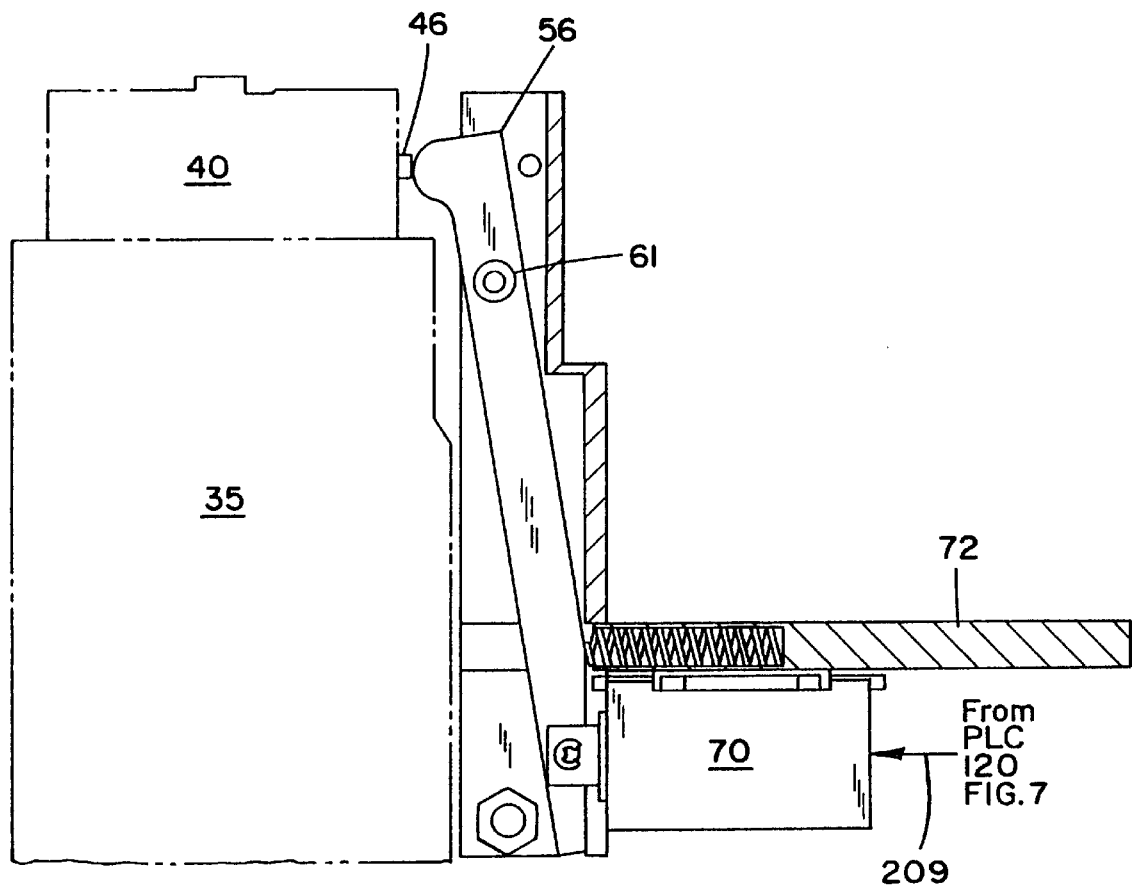
FIG. 7 is a side view of the robot load solenoid that actuates the jaws of the precision conveyor boat.

The Conveyor Initiation Task 190 functions to initiate the Conveyor Indexing Control task 180 and is started whenever the ROBOT ENABLE signal 219 is raised from the PLC 120. Once started, this task requests an INDEX INFEED CONVEYOR 1 (25*a*), signal 237, then waits approximately two (2) seconds, and requests an INDEX INFEED CONVEYOR 2 (25*b*), signal 239, as shown in FIG. 7. The task 190 is then terminated and is not restarted again until the ROBOT ENABLE signal 219 is lowered and raised again.

Task Manager

The Task Manager 240 initializes the software and hardware I/O signals, the global variables, and the vision/robot system tasks. Once the vision/robot system tasks are running, the task manager monitors the integrity and status of each task currently running and the resources that are controlled by these tasks. The status poll signals 247*a*–247*f* are indicated in FIG. 8. The resources are the robot, communication ports, and the I/O signal lines. The Task Manager reports any errors to the PLC, via the SYSTEM FAIL signal 222, and the SCADA node, via the SCADA Node Interface Task 195. The SYSTEM FAIL signal 222 is generated whenever a robot (as detected by the Task Manager) has recognized a gross error which prevents it from continuing operation. This signal is active-low and remains low until the Adept robot is reset. Thus, the PLC must lower the ROBOT ENABLE signal 219 immediately upon receiving this signal.

For gross errors occurring with the vision/robot control software, the Task Manager 240 is utilized to detect and recover from these errors by continuously polling the status and integrity of all steady-state tasks and resources during program execution. If it is determined that a gross error has occurred, the SYSTEM FAIL signal 222 will be raised to the PLC 120 and all tasks except the SCADA Node Interface Task, the Control Panel Task and the Task Manager will be stopped. A code indicating the reason for the last unrecoverable error will be available to the SCADA Node through the SCADA Node Interface Task. In some cases, an error message will be displayed in the Monitor Window of the Adept robot controller. After the SYSTEM FAIL signal is raised, the Task Manager will attempt to correct any problems detected on the robot and notify the operator through the Monitor Window. In most cases, the operator will only need to raise the ROBOT ENABLE signal again to re-set the vision/robot control software.

Control Panel Task

The Control Panel Task 260 presents a mouse controlled panel that allows an operator to access various software "debugging" utilities, to access diagnostics utilities, to control the speed of the robot, and to select new positions that the robot will move to for picking and placing needles. Also, the Control Panel Task allows the operator to stop the vision/robot system tasks from executing.

SCADA Node Interface Task

The SCADA Node Interface task 195 polls the SCADA Node RS-232 interface for messages from the SCADA node. The task will act as slave to SCADA Node requests for Adept and camera set-up procedures necessitated by product changeovers. These requests are valid only when the ROBOT ENABLE signal 219 is deactivated.

Lens Control Task

The Lens Control Task 270 is initiated only when the SCADA node requests a new product to be introduced to the vision system and is executed only as an off-line process. The Lens Control Task 270 accepts the new needle parameters and adjusts the field-of-view size for both cameras to accommodate the new product size. The zoom, focus, and iris lenses are affected by this product introduction, as well as internal vision system parameters, such as gain, binary threshold, and offset, used for imaging. Once the cameras are adjusted, the task is suspended until another new product is introduced to the vision/robot system.

Product Changeover

Prior to enabling the robots to begin the needle infeed process, a Needle Changeover procedure is invoked to inform the Vision and Robot Control tasks of the control system software of the type and size of the needles to be processed. This needle changeover procedure must be completed before making needle batch changes. If a changeover is not completed before the first needle batch run after power-up, an error message will be displayed at the FIX/DMACS (SCADA Node) screen when the robots are enabled and the robots will not run. If a changeover is not completed between different needle batch runs, the vision tasks will not identify any needle being run.

Essentially, an operator of the system enters the needle parameters in appropriate units, e.g., millimeters and degrees at the FIX/DMACS screen of the SCADA task 195 through data lines 229. Such needle parameters for use by the Vision tasks include, the needle radius and the radius tolerance, acceptable needle angles and their tolerances, and, the needle width and the width tolerance.

In addition to inputting needle change parameters for the vision tasks, initial camera set-up parameters associated with the particular batch of needles to be processed are also input through the SCADA Node for use by the system. The software utilizes the information provided by the user via the SCADA Node to automatically adjust the lens for the correct field-of-view size, focus, and zoom parameters prior to enabling the robots.

The Precision Conveyor

FIGS. 6(*a*)–6(*c*) illustrate the precision conveyor boat 40 to which each needle 19 is transferred. Each boat is preferably provided with a pair of jaws; one jaw 47 being fixedly mounted, and the second jaw 49 being slidable within pocket 42. In operation, a push rod 46 is pressed in the direction of the arrow "A" shown in FIG. 6(*c*) to compress spring 52 which retracts the position of the movable jaw 49 in the direction indicated by the arrow "B" to allow for placement of needle 19 within the notch 44 of both jaws. Normally, spring 52 is biased as shown in FIG. 6(*b*) to maintain movable jaw 49 in its engaged position for retaining a needle 19 in the notch 44. It should be understood that any type of releasable engaging mechanism may be provided for releasably retaining a needle 19 on conveyor boat 40, provided that each needle be correctly oriented on its respective boat for subsequent swaging to take place.

FIG. 7 illustrates a robot load solenoid mechanism 70 that is activated by signal line 209 from the PLC 120 each time a needle 19 is being transferred to a precision conveyor boat 40 as described above. The robot load solenoid 70 may be mounted to the precision conveyor by an appropriate mounting plate 72. A sensor mounted on the precision conveyor, is provided to sense the proximity of the precision conveyor boat 40. At such time a conveyor boat is dwelled for transference of a needle 19 thereto, a release arm 56 of the robot load solenoid is actuated by solenoid 70 to pivot about pin 51 to depress push rod 46 and retract the movable jaw 49 to the position illustrated in FIG. 6(c). The robot arm 51 then positions the needle 19 between the jaws 47,49 of conveyor boat 40 for engagement thereof. The release arm 56 is then retracted by spring 78 as the conveyor boat 40 resumes movement.

For automatic swaging to take place at the swaging station it is necessary that the needle be precisely positioned within the notch 44 of engagement jaws 47,49 of the boat 40. This is because the multi-axis gripper generally indicated at step 17 in the system flow chart of FIG. 1, must receive a precisely positioned needle for a suture (not shown) to be placed within the suture receiving end 85 of needle 19. To ensure that each needle is uniformly oriented for transference to the multi-axis gripper of the automatic swaging station, a needle orientation device ("plow") 54 is provided as shown in FIGS. 5(b) and 9(a) to orient each needle while engaged between jaws 47,49 on conveyor boat 40. The plow comprises an elongated arcuate blade 57 protruding from a mounting bracket 58 as best shown in FIGS. 9(a) and 9(b). In the preferred embodiment shown in FIG. 5(b) and FIG. 9(c), the plow is fixedly mounted at one end 48 of the precision conveyor 35 to enable arcuate blade 57 to scoop needle 19 positioned on the conveyor boat 40 while in forward motion. After contact is made, the arcuate portion 87 of the needle 19 is lifted and rolls over the arcuate blade 57 of the plow 54 as shown in FIGS. 9(c) through 9(e). Provision of the plow 54 ensures that each needle conveyed to the suture swaging station is oriented in the same direction.

Figure 10A:
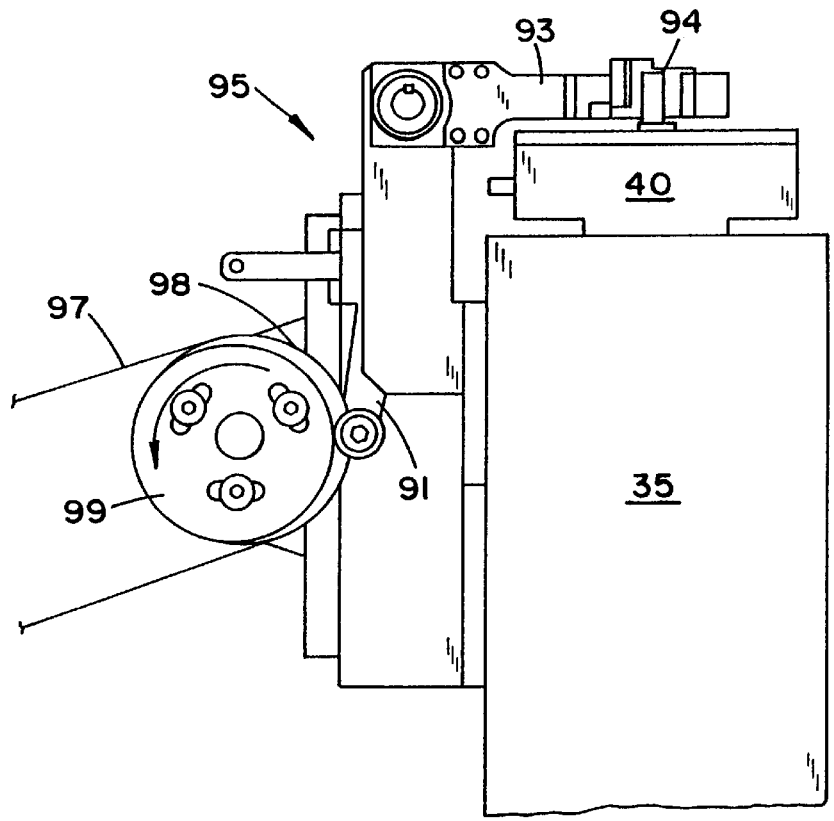
FIG. 10(a) is a side view of the needle pre-positioning assembly 95 which further orients the needle 19 within the engagement jaws of conveyor boat 40.
Figure 10B:
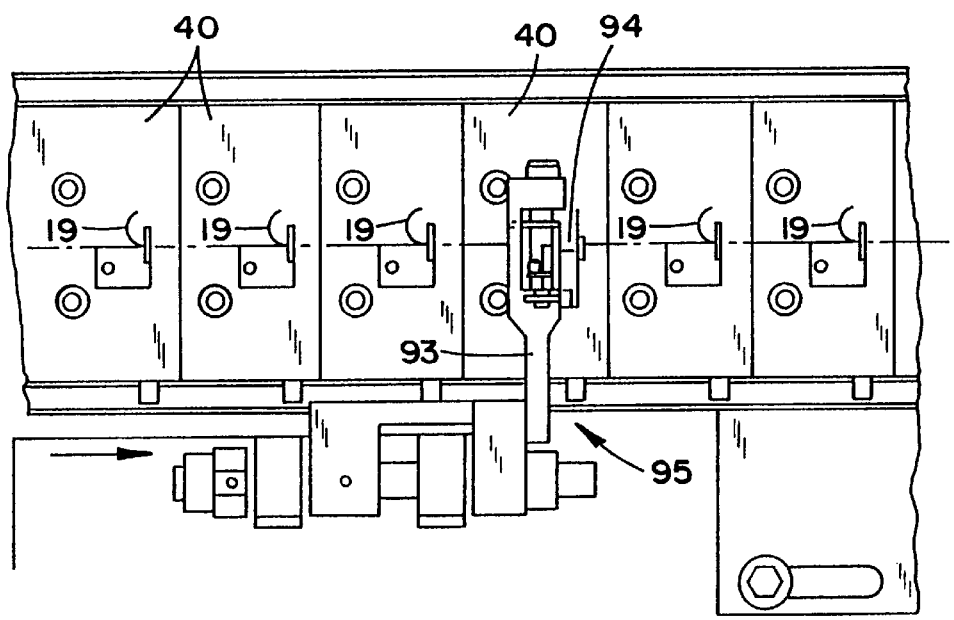
FIG. 10(b) is a top plan view of the needle pre-positioning assembly 95 for further orienting the needle 19 within the engagement jaws of conveyor boat 40.

Another mechanism is provided for further orienting the needle upon the precision conveyor boat is the needle pre-positioning assembly 95 illustrated in FIGS. 10(a) and 10(b). The pre-positioning assembly 95 comprises a pulley 99 operable by a drive motor (not shown) and timing belt 97 for rotating a cam 98 as shown in FIG. 10(a). Cam follower 91 is provided for actuating arm 93 to reciprocate from a first position above the engagement jaws 47,49 of conveyor boat 40, to a position that enables blade 94 of arm 93 to bear upon the end 85 of needle 19 while the precision conveyor boat 40 is conveyed in the forward direction as indicated by the arrow in FIG. 10(b). Impeding the forward motion of the needle 19 by blade 94 forces the needle to move within engagement jaws 47,49 of the conveyor boat 40 so that the engagement jaws 47,49 engage the needle at a precise location, for e.g., its barrel portion 83. Note that the cam 98, as driven by timing belt 97, is designed so that the arm stop 93 reciprocates in a timed relation with the forward motion of the boat 40 as dictated by the Robot Control tasks 150 and PLC 120, so that each needle in each conveyor boat 40 is further pre-positioned and oriented. After the needle is oriented, the arm stop 93 is reciprocated to its position above the conveyor boat 40 to await the next needle for further orientation in the manner heretofore described.

Moveable Hard Stop Assembly

Figure 11A:
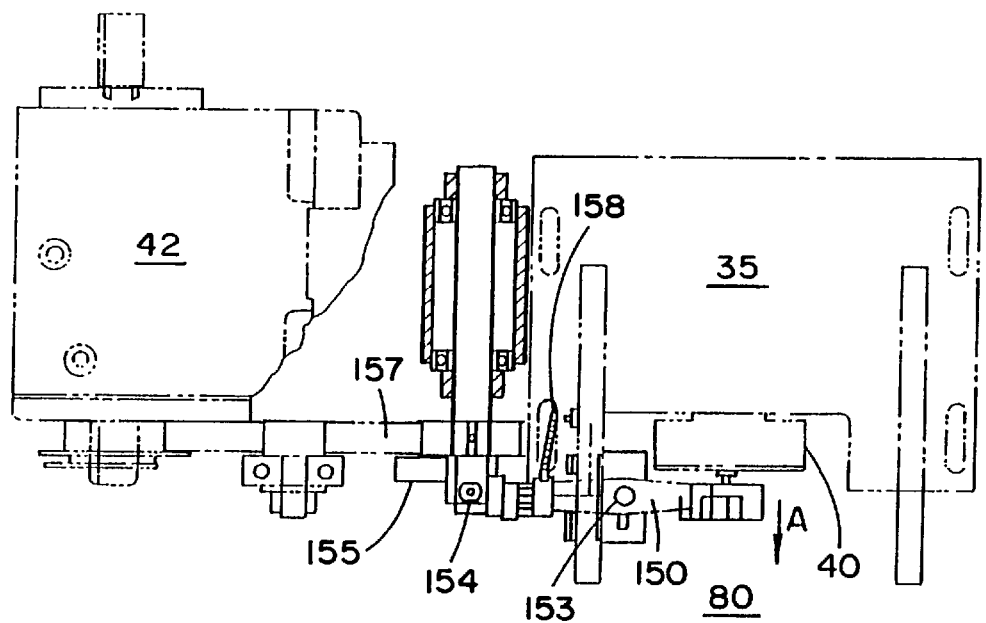
FIG. 11(a) is a plan view of the moveable hard stop assembly 80 for final positioning of the needle 19 in conveyor boat 40.
Figure 11B:
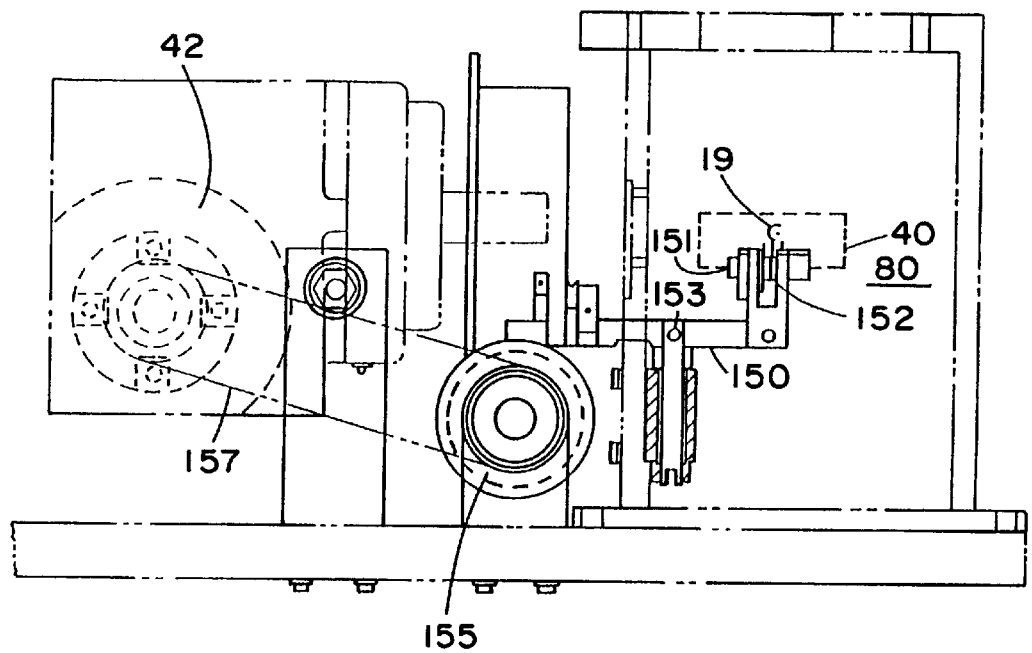
FIG. 11(b) is a front elevation view of the moveable hard stop assembly 80 illustrated in FIG. 11(a).
Figure 13A:
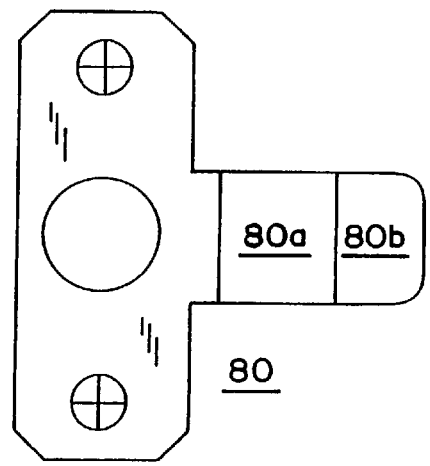
FIG. 13(a) is a top plan view of the hard stop used by the moveable hard stop assembly 80.
Figure 13B:
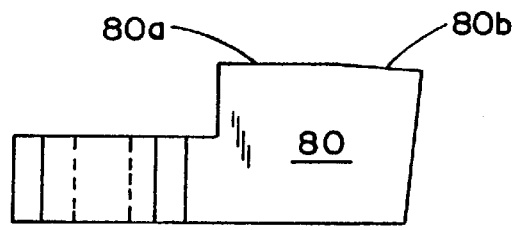
FIG. 13(b) is a side elevation view of the hard stop illustrated in FIG. 13(b).

After the needle 19 has been prepositioned in the conveyor boat 40 as previously described with respect to FIGS. 10a,10b, it is conveyed to an automatic swaging system (not shown) where a suture is inserted into the needle, and the needle swaged about the suture. A moveable hard stop assembly 80 is illustrated in FIGS. 11(a) and 11(b) where FIG. 11(a) is a top or plan view of the apparatus and FIG. 11(b) is an elevation end view of the apparatus. The hard stop assembly illustrated in FIGS. 11a and 11b is the mechanism used for executing a hard stop of the needle conveyed in conveyor boat 40 when the boat has reached the end of its destination at the hand-off point for the needle swaging station. The stop 82 (illustrated in FIGS. 13(a) and 13(b) provides a precise positioning surface for the needle in boat 40. Typically, the hard stop 80 provides positioning within an accuracy of 0.001 inches of a denoted reference position subsequently used for swaging. The hard stop of the present invention differs from the stop 80 described with respect to the parent application inasmuch as the stop 80 in the parent application was a fixed stop mechanism whereas the apparatus illustrated in FIGS. 11a and 11b is a moveable stop mechanism. The moveable stop 80 is reciprocated out of the way to provide clearance for the conveyor boat 40 as it continues its downward travel to return to the opposite end of the conveyor. As the conveyor boat 40 reaches its final position as illustrated in FIG. 11(a) the hard stop 80 is positioned to receive the butt end of the needle on needle face 80a as illustrated in FIG. 13. As the boat 40 arrives at its final location, the gripping jaws of the swage device arrive on the opposite side of the needle hard stop 80. The needle is thus restrained during handoff against downward movement by the hard stop 80, from side-to-side movement by the jaws 47, 49 of the conveyor boat 40 against rearward motion by the conveyor boat 40 and against forward motion by the multi-axis gripper on the swage machine which is to receive the needle. The multi-axis gripper also has a pair of jaws (not shown) which engage the needle to prevent side-to-side motion after transfer is complete, and the jaws 47, 49 are open and the jaws of the multi-axis gripper are closed, the hard stop 80 is reciprocated in the direction of the arrow A in FIG. 11a to provide clearance for movement of jaws 47,49 on boat 40 and for movement of the butt end of the needle as it is moved out of position by the multi-axis gripper. To provide further clearance for the butt end of the needle, and to avoid dislodging it from its precise position, the trailing face of the hard stop 80 is tapered as illustrated at 80b in FIG. 13(b).

The hard stop 80 is spring mounted in a pivot arm 150 by means of a pivot pin 151 and a coil spring 152 which maintains the position of the stop, but provides breakaway capability for the stop in the event of misalignment of the precision conveyor. The breakaway prevents any damage to the conveyor boat 40 from the hard stop 80 in the event of any malfunction of the device. The pivot arm 150 is pivoted about pivot point 153 by means of a guide roller 154 and a face cam 155 which is rotated by the Camco drive motor 42 through belt assembly 157.

Figure 12:
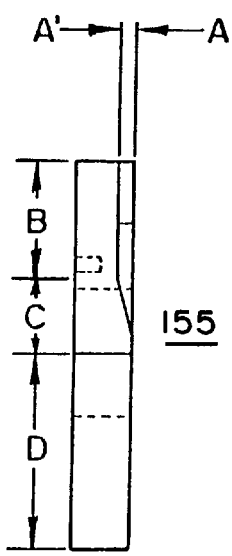
FIG. 12 is a side view of the face cam plate used by the moveable hard stop assembly 80 to retract the hard stop after transfer of the precisely positioned needle.

The face cam 155 is illustrated in FIG. 12 and provides for reciprocal movement of the hard stop mechanism of approximately ⅛ of an inch during each dwell period. The cam surface is illustrated with A–A' being the reciprocal distance, dwell period B, being the retracted dwell period, dwell period D being the engaged dwell period, and C being one of the transition periods. The pivot arm 150 is pulled into engagement with the face cam by means of a tension spring 158. As the face cam 155 is rotated, the hard stop is held in its engagement position for approximately 195° of rotation of the face cam and held in its retracted position for approximately 120° of travel with transition periods therebetween. The ratios of belt drive mechanism 157 are chosen to provide one cycle of rotation for the face cam 155 for each step advance of the conveyor boat 40.

Multi-Axis Gripper

The multi-axis gripper 18 used by the present invention is described in detail in U.S. Pat. No. 5,473,810, and receives the needle from the precision conveyor and moveable hard stop mechanism, and transports the needle through the swage operation in which a suture is automatically inserted into the barrel end of the needle, and the metal of the needle swaged about the suture. As can be appreciated, when the opening in the barrel is only 0.0106 and the suture diameter is 0.0088, a high degree of precision handling is required, particularly so when the insertion and swage operation need to be completed in approximately 0.5 seconds in order to maintain a 60 needle per minute cycle rate. The multi-axis gripper also transports the needle through the pull test station in which the suture bond is tested and to the packaging area, where the armed suture (needle and suture) is either bundled for future packaging, or mounted in an RSO tray such as the trays illustrated in FIGS. 2(a) and 2(b).

Figure 14:
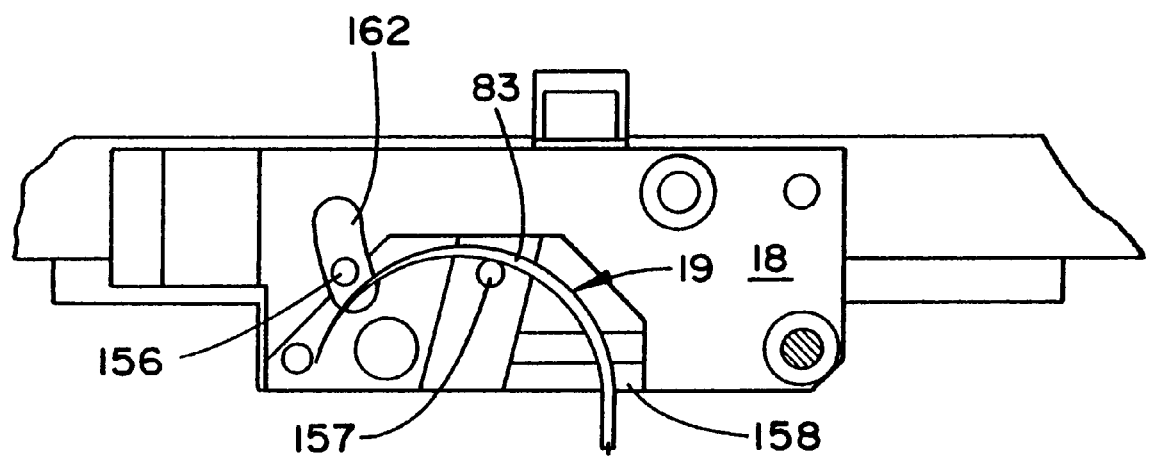
FIG. 14 is an elevation view of the multi-axis gripper of the present invention.

As illustrated in FIG. 14, the gripper portion of the multi-axis gripper is illustrated, with three needle gripping pins 156,157,158, that extend outward from the gripper to engage a portion of the needle 19 therein. Pins 157 and 158 are fixed and pin 156 is reciprocable along channel 162 to grip the needle 19 in a three point gripping engagement. The moveable hard stop 80 provides a precise positioning point for the butt end of the needle 19, and the pins 157, 158 of the multi-axis gripper provide precise arcuate placement for the needle.

In operation, a plurality of multi-axis grippers are employed, each of which grips a single needle for swaging, testing and packaging. Referring to FIGS. 5, 11(a) and 15(a), as the multi-axis gripper is moved into position, the pin 156 is opened and the gripper is reciprocated towards the needle so that open pins are presented on each side of the needle. The jaws 47,49 of the precision conveyor boat are then opened, and during transfer, the needle rests on the moveable hard stop 80. Pin 156 of the multi-axis gripper is then closed to grip the needle and the moveable hard stop is reciprocated out of engagement with the needle, and away from the jaws 47,49 of the precision conveyor to allow the precision conveyor to advance the next needle into the needle transfer position.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

What is claimed:

1. An automatic needle sorting and infeed apparatus for singulating and precisely positioning curved surgical needles for subsequent swaging, said apparatus comprising:
    (a) means for individually singulating a single needle from a bulk supply and depositing a single needle upon a first conveyor means;
    (b) means for obtaining an image of said needles at one or more predetermined locations upon said first conveyor means, said means including digitizing means for converting said image into digital signals;
    (c) computer control means for processing said digital signals to obtain positional and orientation data for each selected one of the imaged needles on said first conveyor means; and
    (d) transfer means for removing said needle from said first conveyor means in accordance with its individual positional and orientation data and transferring said needle to a second precision conveyor for further orientation and precise position;
    (e) a precision transfer station for transferring the needle to a multi-axis gripper for a subsequent swaging operation.

2. The automatic needle sorting and infeed apparatus as claimed in claim 1 wherein said transfer means includes one or more robot means each robot means having a gripper means for picking up needles from said first conveyor means, and placing said needles upon said second conveyance means.

3. The automatic needle sorting and infeed apparatus as claimed in claim 1 wherein said second precision conveyor means includes one or more engagement devices for gripping a respective needle, said transfer means placing each said needle in a respective engagement device.

4. The automatic needle sorting and infeed apparatus as claimed in claim 1 wherein said computer control means further includes memory means for storing said positional and orientation data corresponding to said imaged needles, said transfer means including means for accessing said memory means to obtain said positional and orientation data corresponding to said imaged needles.

5. The automatic needle sorting and infeed apparatus as claimed in claim 1 wherein said means for obtaining an image of said individually deposited needles includes one or more camera means, each of said one or more camera means in communication with said computer control means.

6. The automatic needle sorting and infeed apparatus as claimed in claim 5 wherein each of said camera means obtains a video image of said needles upon said first conveyor means at each of respective said one or more predetermined locations within a field-of-view of each of said one or more camera means.

7. The automatic needle sorting and infeed apparatus as claimed in claim 4 wherein said robot means is in communication with said memory means, said robot means accessing said memory means to obtain said positional and orientation data corresponding to said imaged needles.

8. The automatic needle sorting and infeed apparatus as claimed in claim 3 wherein each of said engagement devices includes a pair of engaging jaws for engaging a needle positioned therebetween by said transfer means.

9. The automatic needle sorting and infeed apparatus as claimed in claim 8 wherein each said engagement device further a includes spring means for biasing a first movable jaw of said pair of engaging jaws into engagement with a second fixed jaw of said pair of engaging jaws to retain said needle positioned therebetween.

10. The automatic needle sorting and infeed apparatus as claimed in claim 9 wherein each of said engagement devices further includes means for retracting said first movable engaging jaw from engagement with said second fixed jaw prior to positioning said needle therebetween.

11. The automatic needle sorting and infeed apparatus as claimed in claim 10 wherein said means for retracting said first movable jaw from engagement with said second fixed jaw is a push rod for pushing said first movable jaw in opposition to said bias of said spring means.

12. The automatic needle sorting and infeed apparatus as claimed in claim 3 further including a first orienting means for orienting each said needle in a uniform direction while positioned upon said precision conveyor means.

13. The automatic needle sorting and infeed apparatus as claimed in claim 12 further including a second orienting means for further orienting said needle axially within said pair of engagement jaws.

14. The automatic needle sorting and infeed apparatus as claimed in claim 13 further including a third orienting means for further orienting said needle to within 0.001 inch of a desired predetermined orientation for said needle upon said second conveyance means.

15. A method for automatically sorting needles comprising the steps of:
  (a) singulating a single needle from a bulk supply of needles and depositing individual needles in a spaced relationship upon a first conveyor means;
  (b) obtaining an image of said deposited needles upon said first conveyor means and digitizing said image;
  (c) processing said digitized image to obtain positional and orientation data for one or more of said deposited needles;
  (d) transferring said selected needle from said first conveyor means to a second precision conveyance means in a predetermined orientation based upon said positional and orientation data;
  (e) precisely positioning said selected needle for transfer to a multi-axis gripper for subsequent automatic swaging.

16. A method according to claim 15 wherein the step (c) of obtaining positional and orientation data for a selected deposited needle further includes the step of processing said positional and orientation data for generating instructions to enable a robot arm means to grasp said selected needle at a preselected location in accordance with its respective positional and orientation data and transfer it to said second conveyance means in a predetermined orientation.

17. A method according to claim 16 wherein the step (d) of transferring the needles further includes the step of placing each needle between a pair of engagement jaws located upon said second precision conveyance means.

18. A method according to claim 17 further including the step of pre-positioning said needle while carried by said pair of engagement jaws on said second precision conveyance means.

19. A method according to claim 18 further including the step reorienting said needle from a horizontal orientation to a vertical orientation, and then releasing said pair of engagement jaws to rest said needle on a moveable hard stop for transfer to a multi-axis gripper.

* * * * *